United States Patent
Kidron et al.

(10) Patent No.: US 10,967,051 B2
(45) Date of Patent: Apr. 6, 2021

(54) METHODS AND COMPOSITIONS FOR TREATING NAFLD, HEPATIC STEATOSIS, AND SEQUELAE THEREOF

(71) Applicant: ORAMED LTD., Jerusalem (IL)

(72) Inventors: Miriam Kidron, Jerusalem (IL); Ehud Arbit, Englewood, NJ (US)

(73) Assignee: Oramed Ltd., Jerusalem (IL)

( * ) Notice: Subject to any disclaimer, the term of this patent is extended or adjusted under 35 U.S.C. 154(b) by 0 days.

(21) Appl. No.: 16/195,184

(22) Filed: Nov. 19, 2018

(65) Prior Publication Data

US 2019/0209655 A1    Jul. 11, 2019

Related U.S. Application Data

(63) Continuation of application No. 14/759,060, filed as application No. PCT/IL2014/050007 on Jan. 2, 2014, now abandoned.

(60) Provisional application No. 61/763,996, filed on Feb. 13, 2013.

(30) Foreign Application Priority Data

Jan. 3, 2013   (WO) .................. PCT/IL2014/050007

(51) Int. Cl.
| | | |
|---|---|---|
| A61K 38/28 | (2006.01) |
| A61K 38/55 | (2006.01) |
| A61K 9/48 | (2006.01) |
| A61K 38/26 | (2006.01) |
| A61K 38/56 | (2006.01) |
| A61K 38/57 | (2006.01) |
| A61K 47/60 | (2017.01) |

(52) U.S. Cl.
CPC ............ *A61K 38/28* (2013.01); *A61K 9/4858* (2013.01); *A61K 9/4875* (2013.01); *A61K 9/4891* (2013.01); *A61K 38/26* (2013.01); *A61K 38/55* (2013.01); *A61K 38/56* (2013.01); *A61K 38/57* (2013.01); *A61K 47/60* (2017.08)

(58) Field of Classification Search
CPC ..................................................... A61K 38/28
See application file for complete search history.

(56) References Cited

U.S. PATENT DOCUMENTS

| | | | |
|---|---|---|---|
| 4,579,730 A | 4/1986 | Kidron et al. |
| 5,034,415 A | 7/1991 | Rubin |
| 5,206,219 A | 4/1993 | Desai |
| 5,665,700 A | 9/1997 | Cho et al. |
| 5,824,638 A | 10/1998 | Burnside et al. |
| 6,525,102 B1 | 2/2003 | Chen et al. |
| 6,692,766 B1 | 2/2004 | Rubinstein et al. |
| 6,761,903 B2 | 7/2004 | Chen et al. |
| 6,858,576 B1 | 2/2005 | Young et al. |
| 7,404,973 B2 | 7/2008 | Konwinski et al. |
| 9,186,412 B2 | 11/2015 | Kidron et al. |
| 9,259,456 B2 | 2/2016 | Kidron |
| 10,010,503 B2 | 7/2018 | Kidron et al. |
| 10,058,593 B2 | 8/2018 | Kidron |
| 10,342,764 B2 | 7/2019 | Hershko et al. |
| 10,350,162 B2 | 7/2019 | Kidron |
| 10,398,762 B2 | 9/2019 | Kidron |
| 10,420,721 B2 | 9/2019 | Kidron et al. |
| 2002/0032171 A1 | 3/2002 | Chen et al. |
| 2003/0118610 A1 | 6/2003 | Stern et al. |
| 2004/0097410 A1 | 5/2004 | Zheng et al. |
| 2005/0143303 A1 | 6/2005 | Quay et al. |
| 2005/0232981 A1 | 10/2005 | Ben-Sasson |
| 2006/0018874 A1 | 1/2006 | Radhakrishnan et al. |
| 2006/0045868 A1 | 3/2006 | Meezan et al. |
| 2006/0045869 A1 | 3/2006 | Meezan et al. |
| 2006/0234913 A1 | 10/2006 | Arbit et al. |
| 2006/0264401 A1 | 11/2006 | Campbell et al. |
| 2006/0286129 A1 | 12/2006 | Sarubbi |
| 2006/0293232 A1 | 12/2006 | Levy et al. |
| 2007/0077283 A1 | 4/2007 | Quay et al. |
| 2007/0086972 A1 | 4/2007 | Birnbaum |
| 2007/0087957 A1 | 4/2007 | Kidron |
| 2008/0274203 A1 | 11/2008 | Bruheim et al. |
| 2009/0312246 A1* | 12/2009 | Baron ................. A61P 3/00 514/1.1 |
| 2009/0312302 A1* | 12/2009 | Currie ................ A61P 1/16 514/210.02 |
| 2011/0014247 A1 | 1/2011 | Kidron |
| 2011/0046053 A1 | 2/2011 | Kidron |
| 2011/0092510 A1 | 4/2011 | Klein et al. |

(Continued)

FOREIGN PATENT DOCUMENTS

| | | |
|---|---|---|
| CA | 1223200 A1 | 6/1987 |
| CA | 2621577 A1 | 3/2007 |

(Continued)

OTHER PUBLICATIONS

Bernkop-Schnurch et al., 1998, Development and In Vitro Evaluation of a Drug Delivery System Based on Chitosan-EDTA BBI Conjugate, Journal of Drug Targeting, 6(3): 207-214.*

(Continued)

*Primary Examiner* — Amber D Steele

(74) *Attorney, Agent, or Firm* — Sterne, Kessler, Goldstein & Fox P.L.L.C.

(57) ABSTRACT

Provided herein are oral pharmaceutical compositions containing a GLP-1 analogue and/or insulin for treating and reducing the incidence of nonalcoholic fatty liver disease (NAFLD), hepatic steatosis, and sequelae thereof, and methods of utilizing same.

19 Claims, No Drawings

Specification includes a Sequence Listing.

(56) References Cited

U.S. PATENT DOCUMENTS

| | | | |
|---|---|---|---|
| 2011/0092592 A1* | 4/2011 | Yano | A61P 3/06 |
| | | | 514/549 |
| 2011/0105510 A1 | 5/2011 | Ishikawa | |
| 2011/0166062 A1 | 7/2011 | DiMarchi et al. | |
| 2011/0166228 A1 | 7/2011 | Holmeide et al. | |
| 2011/0275561 A1 | 11/2011 | Graefe-Mody et al. | |
| 2012/0009259 A1* | 1/2012 | Delaet | A61P 3/08 |
| | | | 424/465 |
| 2012/0122940 A1 | 5/2012 | Hovland et al. | |
| 2012/0165251 A1* | 6/2012 | Klein | A61K 31/522 |
| | | | 514/6.2 |
| 2012/0202849 A1 | 8/2012 | Pareek | |
| 2012/0208836 A1* | 8/2012 | Saltiel | A61P 3/10 |
| | | | 514/291 |
| 2012/0264824 A1 | 10/2012 | Mizuguchi et al. | |
| 2013/0129724 A1* | 5/2013 | Boettcher | C07K 14/605 |
| | | | 424/134.1 |
| 2013/0195939 A1 | 8/2013 | Kidron | |
| 2013/0273154 A1 | 10/2013 | Fayad et al. | |
| 2014/0220134 A1 | 8/2014 | Zierhut et al. | |
| 2014/0377344 A1 | 12/2014 | Hershko et al. | |
| 2015/0017238 A1 | 1/2015 | Kidron | |
| 2015/0335715 A1 | 11/2015 | Kidron et al. | |
| 2016/0206703 A1 | 7/2016 | Kidron | |
| 2018/0369339 A1 | 12/2018 | Kidron | |

FOREIGN PATENT DOCUMENTS

| | | |
|---|---|---|
| CN | 101095942 A | 2/2008 |
| EP | 0351651 A2 | 1/1990 |
| IL | 68769 A | 2/1986 |
| JP | 02-250823 A | 10/1990 |
| JP | 09/208485 A | 8/1997 |
| JP | 10-330287 A | 12/1998 |
| JP | 00/050793 A | 2/2000 |
| JP | 2001/240558 A | 9/2001 |
| JP | 2005-525308 A | 8/2005 |
| JP | 2011-515458 A | 10/2009 |
| KR | 2001/0069322 A | 7/2001 |
| KR | 2001/0069433 A | 7/2001 |
| RU | 2104715 C1 | 2/1998 |
| WO | WO 91/14454 A1 | 10/1991 |
| WO | WO 97/03688 A1 | 2/1997 |
| WO | WO 00/24424 A1 | 7/2000 |
| WO | WO 2003/057170 A2 | 7/2003 |
| WO | WO 2007/029238 A2 | 3/2007 |
| WO | WO 2009/118722 A2 | 10/2009 |
| WO | WO 2009/136392 A2 | 11/2009 |
| WO | WO 2011/082338 A1 | 7/2011 |

OTHER PUBLICATIONS

Nakajima, 2012, Multidisciplinary Pharmacotherapeutic Options for Nonalcoholic Fatty Liver Disease, International Journal of Hepatology, 2012: 13 pages.*
Carulli et al., 2013, Classical and Innovative Insulin Sensitizing Drugs for the Prevention and Treatment of NAFLD, Current Pharmaceutical Design, 19: 17 pages.*
Gariani et al., 2013, Non-alcoholic fatty liver disease and insulin resistance: From bench to bedside, Diabetes & Metabolism, 39: 16-26.*
Papa et al., 2012, Factors that influence basal insulin requirement in type 2 diabetes, Acta Diabetol, 49: 387-393.*
Smith et al., 2011, Non-alcoholic fatty liver disease, Critical Reviews in Clinical Laboratory Sciences, 48(3): 97-113.*
Williams et al., 2013, Diabetes and Nonalcoholic Fatty Liver Disease: A Pathogenic Duo, Endocrine Reviews, 34(1): 84-129.*
Polyzos et al., 2012, Nonalcoholic Fatty Liver Disease, J Clin Gastroenterol, 46(4): 272-284.*
Shyangdan et al., 2011, Insulin sensitizers in the treatment of non-alcoholic fatty liver disease: a systematic review, Health Technology Assessment, 15(38): 132 pages.*

International Search Report and Written Opinion for Application No. PCT/IL2014/050007 dated Dec. 10, 2014.
International Preliminary Report on Patentability for Application No. PCT/IL2014/050007 dated Jul. 16, 2015.
[No Author Listed] Cure Talk (retrieved from http://trialx.com/curetalk/2012/05/type-2-diabetes-difficult-to-treat-in-children-new-study/ on Apr. 22, 2015, 2 pages).
[No Author Listed] Joslin Diabetes Center (retrieved from http://www.joslin.org/info/will diabetes go away.html on Apr. 22, 2015, 2 pages).
[No Author Listed] Sigma-Aldrich, 2017. T9128. Trypsin inhibitor from Glycine max (soybean). At www.sigmaaldrich.com/catalog/product/sigma/t9128?lang+en®ion=US; revised Aug. 12, 2015; printed Jan. 23, 2017.
[No Author Listed] The Observer (retrieved from http://observer.com/2014/02/tough-to-swallow-paper-trail-breakthrough-leads-to-penny-stock-profiteers/ on Apr. 22, 2015, 5 pages).
[No Author Listed] WebMD (retrieved from http://www.webmd.com/diabetes/is-there-a-diabetes-cure on Apr. 22, 2015, 3 pages).
[No Author Listed] Worthington Biochemical Corporation (2016; Trypsin inhibitors C.A.S.: 9035-81-1. On the web at worthington-biochem.com/TI/default.html.
Agarwal, et al.; Oral Delivery of Proteins: Effect of Chicken and Duck Ovomucoid on the Stability of Insulin in the Presence of a-Chymotrypsin and Trypsin; Pharm. Pharmacal. Commun.; (2000); 6: 223-227.
Bar-On, H., et al.; Enteral Administration of Inslin in the Rat; Br. J. Pharmac. (1981); 73: 21-24.
Bendayan, et al.; Biochemical and morpho-cytochemical evidence for the intestinal absorption of insulin in control and diabetic rats. Comparison between the effectiveness of duodenal and colon mucosa; Diabetologia (1994); 37: 119-126.
Bendayan, et al.; Morpho-cytochemical and biochemical evidence for insulin absorption by the rat ileal epithelium; Diabetologia (1990); 33: 197-204.
Birk, Trypsin and chymotrypsin inhibitors from soybeans. Methods Enzymol. 1976;45:700-7.
Carino, et al.; Oral insulin delivery; Advanced Drug Delivery Review (1999); 35: 249-257.
Cernea, et al.; Comparison of pharmacokinetic and pharmacodynamic properties of single-dose oral insulin spray and subcutaneous insulin injection in healthy subjects using the euglycemic clamp technique; Clinical Therapeutics (2004); 26(12): 2084-2091.
Cernea, et al.; Dose-Response Relationship of an Oral Insulin Spray in Six Patients with Type 1 Diabetes: A Single-Center, Randomized, Single-Blind, 5-Way Crossover Study; Clinical Therapeutics (2005); 27(10): 1562-1570.
Cernea, et al.; Dose-Response Relationship of Oral Insulin Spray in Healthy Subjects; Diabetes Care (2005); 28(6): 1353-1357.
Chiquette et al., Treatment with exenatide once weekly or twice daily for 30 weeks is associated with changes in several cardiovascular risk markers. Vase Health Risk Manag.2012;8:621-9. doi: 10.2147NHRM.S37969. Epub Nov. 12, 2012.
Cole, et al.; Challenges and opportunities in the encapsulation of liquid and semi-solid formulations into capsules for oral administration; Advanced Drug Delivery Reviews (2008); 60:747-756.
Cournarie, et al.; Insulin-loaded W/0/W multiple emulsions: comparison of the performances of systems prepared with medium-chain-triglycerides and fish oil; Euro. J. of Pharmaceutics and BioPharmaceutics; (2004); 58(3): 477-482.
Eldor et al., A Single-Blind, Two-Period Study to Assess the Safety and Pharmacodynamics of an Orally Delivered GLP-1 Analog (Exenatide) in Healthy Subjects, American Diabetes Association 70th Annual Scientific Sessions, Jun. 25-29, 2010A, Orlando, Florida.
Eldor et al., Open-label study to assess the safety and pharmacodynamics of five oral insulin formulations in healthy subjects. Diabetes Obes Metab. Mar. 2010;12(3):219-23. doi:10.1111/j.1463-1326.2009.01153.x.
Eldor et al., Novel glucagon-like peptide-1 analog delivered orally reduces postprandial glucose excursions in porcine and canine models. J Diabetes Sci Technol. Nov. 1, 2010;4(6):1516-23.

(56) References Cited

OTHER PUBLICATIONS

Gershanik et al., Self dispersing lipid formulations for improving oral absorption of lipophilic drugs. European Journal of Pharmaceutics and Biopharmaceutics. 2000;50:179-188.
Gowthamarajan & Kulkarni; Oral Insulin—Fact or Fiction-Possibilities of Achieving Oral Delivery for Insulin; Resonance (2003); 38-46.
Griffin, Calculation of HLB Values of Non-Ionic Surfactants. J Soc Cosmetic Chemists 5:259 (1954).
Hays, et al.; Prevention and Treatment of Type 2 Diabetes: Current Role of Lifestyle, Natural Product, and Pharmacological Interventions; Pharmacal. Ther. (2008); 118(2):181-191.
Heine, et al.; Exenatide versus Insulin Glargine in Patients with Suboptimally Controlled Type 2 Diabetes; American College of Physicians-Annals of Internal Medicine 2005; 143(8): 559-569.
Iyer, et al.; Oral insulin—a review of current status; Diabetes, Obesity and Metabolism (2010); 12: 179-185.
Kidron, et al.; A novel per-oral insulin formulation: proof of concept study in non-diabetic subjects; Diabetic Medicine (2004); 21: 354-357.
Kidron, et al., Extended exposure to an oral insulin formulation yields decreased insulin secretion in Type II diabetes subjects; Diabetes Technology Meeting Nov. 11-13, 2010, Bethesda, MD.
Koide et al., Studies on soybean trypsin inhibitors. 3. Amino-acid sequences of the carboxyl-terminal region and the complete amino-acid sequence of soybean trypsin inhibitor (Kunitz). Eur J Biochem. Feb. 1, 1973;32(3):417-31.
Koide et al., The amino acid sequence of soybean trypsin inhibitor. J. Biochem. Jan. 1972;71(1):165-7.
Kunitz et al., Crystalline soybean trypsin inhibitor: II. General Properties. J Gen Physiol. Mar. 20, 1947;30(4):291-310.
Lasserson, et al.; Optimal insulin regimens in type 2 diabetes mellitus: systematic review and meta-analyses; Diabetologia (2009); 52: 1990-2000.
Li and Deng; Oil-based formulation for oral delivery of insulin; J. Pharmacy Pharmacol 2004; 56: 1101-1107.
Ma, et al.; In vitro and in vivo evaluation of a novel oral insulin formulation; Acta Pharmacologica Sinica (2006); 27(10): 1382-1388.
Mack, et al. Antiobestiy action of peripheral exenatide (exendin-4) in rodents: effects on food intake, body weight, metabolic status and side-effect measures; International Journal of Obesity (2006); 30: 1332-1340.
Maher, S. et al.; Safety and efficacy of sodium caprate in promoting oral drug absorption: from in vitro to the clinic; Advanced Drug Delivery Reviews; (2009); 61: 1427-1449.
Martinez-Colubi et al., Switching to darunavir/ritonavir monotherapy (DRV/r mx): effect on kidney function and lipid profile. J Int AIDS Soc. Nov. 11, 2012;15(6):18348. doi:10.7448/IAS.15.6.18348.
Miyagawa, Jun-ichiro; Med Sci Digest 2008 34(4):147-150.
Miyashita et al., Hepatoprotective effect of tamoxifen on steatosis and non-alcoholic steatohepatitis in mouse models. J Toxicol Sci. Oct. 2012;37(5):931-42.
Morishita et al.; Hypoglycemic effect of novel oral microspheres of insulin with protease inhibitor in normal and diabetic rats; Int. J. of Pharma; (1992); 78: 9-16.
Morishita et al., Novel oral microspheres of insulin with protease inhibitor protecting from enzymatic degradation. International Journal of Pharmaceutics 78 (1992) 1-7.
Nadeau et al., Treatment of non-alcoholic fatty liver disease with metformin versus lifestyle intervention in insulin-resistant adolescents. Pediatr Diabetes. Feb. 2009;10(1):5-13. doi: 10.1111/j.1399-5448.2008.00450.x. Epub Aug. 20, 2008.
Nissan, et al.; Intestinal absorption of low molecular weight heparin in animals and human subjects; Haemostasis (2000); 30: 225-232.
Onuki, et al.; In vivo effects of highly purified docosahexaenoic acid on rectal insulin absorption; Int. J. of Pharmaceutics; (2000); 198(2): 147-156.
Ozawa et al., The reactive site of trypsin inhibitors. J. Biol Chem. Sep. 10, 1966;241(17):3955-61.

Park et al., Oral protein delivery: Current status and future prospect. Reactive and Functional Polymers. 71 (2011) 280-287.
Ray Dirks Research; Novo Nordisk Sitting on $2 Billion in Cash May Look to Acquire Oramed or ISIS for Oral Insulin; May 31, 2012.
Raz, et al.; Rectal Administration of Insulin; Israel Journal of Medical Sciences (1984); 20: 173-175.
Ryan et al., Assessment of the severity of hypoglycemia and glycemic lability in type 1 diabetic subjects undergoing islet transplantation. Diabetes. Apr. 2004;53(4):955-62.
Sherman, Oramed Enrolls First Patient in its Phase 2a U.S. Oral Insulin Clinical Trial; Oramed Pharmaceuticals Inc. Press Release Jul. 8, 2013.
Shyangdan et al., Insulin sensitisers in the treatment of non-alcoholic fatty liver disease: a systematic review. Health Technol Assess. Nov. 2011;15(38):1-110. doi: 10.3310/htal5380.
Siepmann et al., Blends of aqueous polymer dispersions used for pellet coating: importance of the particle size. J Control Release. Jul. 20, 2005;105(3):226-39.
Silva-Cunha et al.; W/O/W multiple emulsions of insulin containing a protease inhibitor and an absorption enhancer: preparation, characterization and determination of stability towards proteases in vitro; Int. J. of Pharmaceutics; (1997); 158(1): 79-89.
Sprecher et al., Molecular cloning, expression, and partial characterization of two novel members of the ovalbumin family of serine proteinase inhibitors. J Biol Chem. Dec. 15, 1995;270(50):29854-61.
Sun et al., Gene structure, chromosomal localization, and expression of the murine homologue of human proteinase inhibitor 6 (PI-6) suggests divergence of PI-6 from the ovalbumin serpins. J Biol Chem. Jul. 7, 1995;270(27):16089-96.
Tesauro et al., Effects of GLP-1 on forearm vasodilator function and glucose disposal during hyperinsulinemia in the metabolic syndrome. Diabetes Care. Mar. 2013;36(3):683-9. doi: 10.2337/dc12-0763. Epub Oct. 15, 2012.
Umezaw A, Structures and activities of protease inhibitors of microbial origin. Methods Enzymol. 1976;45:678-95.
Yeboah et al., A rapid purification method for soybean Bowman-Birk protease inhibitor using hydrophobic interaction chromatography. Protein Expression and Purification. 1996;7:309-14.
Ziv, et al.; Absorption of Protein via the Intestinal Wall a Quantitative Model; Biochemical Pharmacology (1987); 36(7): 1035-1039.
Ziv, et al.; Bile Salts Promote the Absorption of Insulin from the Rat Colon; Life Sciences (1981); 29: 803-809.
Ziv, et al.; Oral administration of insulin in solid form to nondiabetic and diabetic dogs; Journal of Pharmaceutical Sciences (1994); 83(6): 792-794.
Communication pursuant to Article 94(3) EPC for EP Appl. 14 735 143.1, dated Nov. 27, 2017, European Patent Office, Munich, Germany.
Bernkop-Schnurch, Andreas (Pharmaceutical Research 15(2), 263-269, 1998).
Bernkop-Schnurch, 1998, The use of inhibitory agents to overcome the enzymatic barrier to perorally administered therapeutic peptides and proteins, Journal of Controlled Release, 52: 1-16.
Krauland et al., 2004, oral insulin delivery; the potential of thiolated chitosan-insulin tablets on non-diabetic rats, Journal of Controlled Release, 95: 547-555.
Marschutz et al., 2000, Oral peptide drug delivery: polymer-inhibitor conjugates protecting insulin from enzymatic degradation in vitro, Biomaterials, 21: 1499-1507.
Park et al., 2007, Characterization of human insulin microcrystals and their absorption enhancement by protease inhibitors in rat lungs, International Journal of Pharmaceutics, 339: 205-212.
Hirose, T., "Development of new basal insulin peglispro (LY2605541) ends in a disappointing result," Diabetol Int. Jan. 29, 2016;7(1):16-17. doi: 10.1007/s13340-016-0255-1.
Ginsberg H, et al., "Lipid changes during basal insulin peglispro, insulin glargine, or NPH treatment in six IMAGINE trials," Diabetes Obes Metab. Nov. 2016;18(11):1089-1092. doi: 10.1111/dom. 12754. Epub Sep. 14, 2016.

(56) References Cited

OTHER PUBLICATIONS

Buse, JB et al. Randomized Clinical Trial Comparing Basal Insulin Peglispro and Insulin Glargine in Patients With Type 2 Diabetes Previously Treated With Basal Insulin: Diabetes Care. Jan. 2016;39(1):92-100. doi: 10.2337/dc15-1531. Epub Nov. 17, 2015.

Donadon, V et al., "Antidiabetic therapy and increased risk of hepatocellular carcinom in chronic liver disease." World J Gastroenterol. May 28, 2009;15(20):2506-11. doi: 10.3748/wjg.15.2506.

* cited by examiner

SEQUENCE LISTING

<160> NUMBER OF SEQ ID NOS: 4

<210> SEQ ID NO 1
<211> LENGTH: 100
<212> TYPE: PRT
<213> ORGANISM: Bos taurus

<400> SEQUENCE: 1

```
Met Lys Met Ser Arg Leu Cys Leu Ser Val Ala Leu Leu Val Leu Leu
1               5                   10                  15

Gly Thr Leu Ala Ala Ser Thr Pro Gly Cys Asp Thr Ser Asn Gln Ala
            20                  25                  30

Lys Ala Gln Arg Pro Asp Phe Cys Leu Glu Pro Pro Tyr Thr Gly Pro
        35                  40                  45

Cys Lys Ala Arg Ile Ile Arg Tyr Phe Tyr Asn Ala Lys Ala Gly Leu
    50                  55                  60

Cys Gln Thr Phe Val Tyr Gly Gly Cys Arg Ala Lys Arg Asn Asn Phe
65                  70                  75                  80

Lys Ser Ala Glu Asp Cys Met Arg Thr Cys Gly Gly Ala Ile Gly Pro
                85                  90                  95

Trp Glu Asn Leu
            100
```

<210> SEQ ID NO 2
<211> LENGTH: 110
<212> TYPE: PRT
<213> ORGANISM: Glycine max

<400> SEQUENCE: 2

```
Met Val Val Leu Lys Val Cys Leu Val Leu Leu Phe Leu Val Gly Gly
1               5                   10                  15

Thr Thr Ser Ala Asn Leu Arg Leu Ser Lys Leu Gly Leu Leu Met Lys
            20                  25                  30

Ser Asp His Gln His Ser Asn Asp Asp Glu Ser Ser Lys Pro Cys Cys
        35                  40                  45

Asp Gln Cys Ala Cys Thr Lys Ser Asn Pro Pro Gln Cys Arg Cys Ser
    50                  55                  60

Asp Met Arg Leu Asn Ser Cys His Ser Ala Cys Lys Ser Cys Ile Cys
65                  70                  75                  80

Ala Leu Ser Tyr Pro Ala Gln Cys Phe Cys Val Asp Ile Thr Asp Phe
```

```
                        85                  90                  95

Cys Tyr Glu Pro Cys Lys Pro Ser Glu Asp Asp Lys Glu Asn
                100                 105                 110

<210> SEQ ID NO 3
<211> LENGTH: 216
<212> TYPE: PRT
<213> ORGANISM: Glycine max

<400> SEQUENCE: 3

Met Lys Ser Thr Ile Phe Phe Leu Phe Leu Phe Cys Ala Phe Thr Thr
1               5                   10                  15

Ser Tyr Leu Pro Ser Ala Ile Ala Asp Phe Val Leu Asp Asn Glu Gly
            20                  25                  30

Asn Pro Leu Glu Asn Gly Gly Thr Tyr Tyr Ile Leu Ser Asp Ile Thr
        35                  40                  45

Ala Phe Gly Gly Ile Arg Ala Ala Pro Thr Gly Asn Glu Arg Cys Pro
    50                  55                  60

Leu Thr Val Val Gln Ser Arg Asn Glu Leu Asp Lys Gly Ile Gly Thr
65                  70                  75                  80

Ile Ile Ser Ser Pro Tyr Arg Ile Arg Phe Ile Ala Glu Gly His Pro
                85                  90                  95

Leu Ser Leu Lys Phe Asp Ser Phe Ala Val Ile Met Leu Cys Val Gly
                100                 105                 110

Ile Pro Thr Glu Trp Ser Val Val Glu Asp Leu Pro Glu Gly Pro Ala
            115                 120                 125

Val Lys Ile Gly Glu Asn Lys Asp Ala Met Asp Gly Trp Phe Arg Leu
    130                 135                 140

Glu Arg Val Ser Asp Asp Glu Phe Asn Asn Tyr Lys Leu Val Phe Cys
145                 150                 155                 160

Pro Gln Gln Ala Glu Asp Asp Lys Cys Gly Asp Ile Gly Ile Ser Ile
                165                 170                 175

Asp His Asp Asp Gly Thr Arg Arg Leu Val Val Ser Lys Asn Lys Pro
            180                 185                 190

Leu Val Val Gln Phe Gln Lys Leu Asp Lys Glu Ser Leu Ala Lys Lys
        195                 200                 205

Asn His Gly Leu Ser Arg Ser Glu
    210                 215

<210> SEQ ID NO 4
<211> LENGTH: 39
<212> TYPE: PRT
<213> ORGANISM: Heloderma suspectum
<220> FEATURE:
<221> NAME/KEY: MISC_FEATURE
<222> LOCATION: (39)..(39)
<223> OTHER INFORMATION: residue is amidated on C-terminus

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

METHODS AND COMPOSITIONS FOR TREATING NAFLD, HEPATIC STEATOSIS, AND SEQUELAE THEREOF

FIELD

Provided herein are oral pharmaceutical compositions containing a GLP-1 analogue and/or insulin for treating and reducing the incidence of nonalcoholic fatty liver disease (NAFLD), hepatic steatosis, and sequelae thereof.

BACKGROUND

The incretin hormone Glucagon-like Peptide 1 (GLP-1), secreted within minutes of food ingestion, is associated with induction of insulin release. GLP-1 is used in therapies for Type 2 Diabetes Mellitus (T2DM).

Clinical use of the native GLP-1 is limited due to its rapid enzymatic inactivation, resulting in a half-life of 2-3 minutes. To overcome this obstacle, long-acting, degradation-resistant peptides, both natural and synthetic, referred to as GLP-1 mimetic agents or analogues, have been designed and are being used.

Non-alcoholic fatty liver disease (NAFLD) is a spectrum of chronic diseases including fatty liver, or bland steatosis, and sequelae of bland steatosis, such as non-alcoholic steatohepatitis (NASH), lobular necroinflammation with fibrosis, and cirrhosis (Sharma et al, 2011; Puri et al, 2008). NAFLD-related cirrhosis can lead to end-stage liver disease and hepatocellular carcinoma (HCC). Like other chronic end-stage liver diseases, the major option for afflicted persons is liver transplantation. NAFLD appears to be associated with certain dyslipidemias (Malhi et al, 2008; Retnakaran R et al 2012; Sung et al, 2012). An important component of Western diets includes both saturated fatty acids as well as trans-saturated fatty acids. Recent evidence indicates that such fatty acids are partly responsible for inducing steatosis and fueling hepatocyte insulin resistance (Centis et al, 2010).

Some studies have suggested that GLP-1 reduces fat load in hepatocytes and may be useful in treating NAFLD, although other studies have demonstrated that GLP-1 increases hepatic glycogen synthase activity, which is expected to aggravate NAFLD. Indeed, even the very presence of GLP-1 receptor in liver cells remains controversial (Nielsen et al 2008, Redondo et al, 2003; Lopez-Delgado et al, 1998; Sharma et al, 2011; Ben-Shlomo et al 2011). A more rigorous assessment of inflammation and fibrosis in response to GLP-1 is considered necessary in order to more fully understand the response of liver cells to these agents (Kim et al, 2012).

Alzheimer's disease (AD), also known as Alzheimer disease, is the most common form of dementia. There is no cure for the disease, which worsens as it progresses and eventually leads to death. Most often, AD is diagnosed in people over 65 years of age, although the less-prevalent early-onset Alzheimer's can occur much earlier. In 2006, there were 26.6 million sufferers worldwide. The causation of AD is not well understood, although it is typically correlated with accumulation of amyloid β peptides and tau protein in the brain, and these substances are believed by many scientists to play a role in causation.

Parkinson's disease (PD; also known as idiopathic or primary parkinsonism, hypokinetic rigid syndrome/HRS, or paralysis agitans) is a degenerative disorder of the central nervous system. The motor symptoms of Parkinson's disease result from the death of dopamine-generating cells in the substantia nigra, a region of the midbrain, the cause of which is unknown. The disease course typically presents with movement-related symptoms, with thinking and behavioral problems arising later and dementia occurring in advanced disease. Parkinson's disease is more common in older people, with most cases occurring after the age of 50.

Huntington's disease (HD) is a neurodegenerative genetic disorder that affects muscle coordination and leads to cognitive decline and psychiatric problems. It typically becomes noticeable in mid-adult life. The huntingtin gene provides the genetic information for a protein that is also called "Huntingtin". Expansion of a CAG triplet repeat stretch within huntingtin results in a mutant form of the protein, which gradually damages cells in the brain, through mechanisms that are not fully understood.

Amyotrophic lateral sclerosis (ALS), also known as Lou Gehrig's disease and motor neuron disease, is an incurable neurodegenerative disorder of the voluntary motor system. Characterized by selective and progressive death of motor neurons within the brain and spinal cord, it leads to paralysis of voluntary muscles and, eventually, death within five years of clinical onset. Most cases of ALS occur sporadically with unknown etiology (Li et al).

Traumatic brain injury (TBI) affects 1.7 million Americans each year and is a primary contributing factor (30.5%) of all injury-related deaths in the United States. The elderly, in particular, are vulnerable to TBI and suffer an increased mortality and worse functional outcome in the face of lower initial injury severity. Many survivors experience prolonged or even permanent neurocognitive dysfunction, with lasting changes in cognition, motor function, and personality (Eakin et al).

Mood disorders (e.g. bipolar disorder (BD) and major depressive disorder (MDD)) are highly prevalent, affecting 10-15% of the population at some time in their life. Mood disorders are also associated with a range of cognitive deficits which often persist during euthymic states in both treated and untreated individuals. Cognitive deficits are documented across most domains of function, including but not limited to, deficits in learning, memory (e.g., working memory, episodic memory, and semantic memory), attention, executive function, processing speed, and social cognition. However, conventional pharmacological agents for mood disorders are not proven to be sufficiently effective in treating objectively and/or subjectively measured cognitive deficits (McIntyre et al).

Cerebral stroke is caused by blockage or rupture of a blood vessel, which causes a disruption in blood flow to the surrounding tissues. The tissues in the area of the stroke can become irreversibly damaged and ultimately become necrotic and die. While this cell death and resulting brain damage may not be preventable, there is a region of tissue that may be amenable to therapeutic manipulation in the area surrounding the damaged stroke infarct zone (Salcedo et al).

Diabetic retinopathy, one form of retinal degeneration, is damage to the retina caused by complications of diabetes, which can eventually lead to blindness. It is an ocular manifestation of diabetes, a systemic disease, which affects up to 80 percent of all patients who have had diabetes for 10 years or more (Kertes et al).

Peripheral neuropathy (PN) is damage or disease of nerves of the peripheral nervous system. It may affect sensation, movement, gland or organ function, and other aspects of health, depending on the type of nerve affected. PN may be caused by systemic diseases such as diabetes or leprosy, vitamin deficiency, medication (e.g., chemotherapy), traumatic injury, excessive alcohol consumption, immune system disease, or infection, or may be inherited (Hughes).

To date, GLP-1 analogues are only available as injectable dosage forms. The present inventors are developing an oral exenatide (a GLP-1 analogue) formulation for use in treating diabetes. A first-in-humans trial (n=4) testing its safety in healthy humans demonstrated biological functionality of orally delivered exenatide (Eldor et al 2010).

SUMMARY

Provided herein are oral pharmaceutical compositions containing a GLP-1 analogue and/or insulin for treating and preventing nonalcoholic fatty liver disease (NAFLD), hepatic steatosis, and sequelae thereof, and methods of utilizing same. Results from subcutaneous, systemic, and other routes of administration cannot be extrapolated to oral administration, since oral dosage forms tend to utilize the portal route of absorption. To the knowledge of the inventors, orally administered GLP-1 analogues have never been tested for treatment of NAFLD, sequelae thereof, or neurodegenerative disease.

It is described herein that the described compositions are capable of treating and preventing sequelae of NAFLD, as well as other therapeutic effects mediated by GLP-1 receptors outside the pancreas. Accordingly, the described compositions are capable of treating and preventing obesity, elevated total cholesterol, hypertriglyceridemia, elevated serum ApoB levels, elevated total cholesterol/HDL ratios, and elevated ApoB/ApoA1 ratios, atherosclerosis, sub-clinical inflammation, a prothrombotic state, platelet activation, endothelial dysfunction, a cardioembolic state, and impaired insulin-induced enhancement of vasodilator responses (Sung et al, 2012; Chatrath et al 2012; Nseir et al, 2011; Salcedo et al, 2012). It is also described that the described compositions are capable of treating various neurodegenerative disorders.

Also provided herein are solid pharmaceutical compositions for administration of a therapeutic protein to a subject.

The terms "protein" and "peptide" are used interchangeably herein. Neither term is intended to confer a limitation of the number of amino acids present, except where a limitation is explicitly indicated.

Unless indicated otherwise, all ranges mentioned herein are inclusive.

DETAILED DESCRIPTION OF THE EMBODIMENTS

Provided herein is a pharmaceutical composition for treating or reducing the incidence of nonalcoholic fatty liver disease (NAFLD) in a human, said pharmaceutical composition comprising a GLP-1 analogue, at least one protease inhibitor, and a chelator of divalent cations. In another embodiment, the pharmaceutical composition comprises a GLP-1 analogue, insulin, at least one protease inhibitor, and a chelator of divalent cations. In still other embodiments, the pharmaceutical composition comprises insulin, at least one protease inhibitor, and a chelator of divalent cations. In certain embodiments, the pharmaceutical composition is administered to the subject for an extended time.

In some embodiments, the pharmaceutical compositions described herein are solid formulations. In other embodiments, the described pharmaceutical compositions comprise a liquid formulation, wherein said formulation is, in certain embodiments, surrounded by a capsule and/or a coating that resists degradation in the stomach. In some embodiments, the liquid formulation is an oil-based liquid formulation. Some embodiments of the liquid formulation comprise a GLP-1 analogue, insulin, at least one protease inhibitor, examples of which are trypsin inhibitors and chymotrypsin inhibitors, and a chelator of divalent cations. In other embodiments, the liquid formulation comprises a GLP-1 analogue, at least one protease inhibitor, and a chelator of divalent cations. In other embodiments, the liquid formulation comprises insulin, at least one protease inhibitor, and a chelator of divalent cations. Each described embodiment regarding the GLP-1 analogue and amount thereof, insulin and amount thereof, protease inhibitors, chelators, coatings, etc, is also intended to be considered a specific embodiment in the context of liquid formulations in general and oil-based liquid formulations in particular and also in the context of the solid formulations described herein. Those skilled in the art will appreciate, in light of the present disclosure, that solid dosage forms may comprise a different list of inactive excipients from the described liquid formulations.

In some embodiments, the subject receiving the described pharmaceutical composition already has NAFLD. In other embodiments, the subject is at risk of developing NAFLD.

In yet another aspect, a use of a combination of ingredients described herein is provided in the preparation of a medicament for treating NAFLD in a human.

Still another aspect provides a method for treating or reducing the incidence of NAFLD in a human, the method comprising the optional step of selecting a subject by diagnosing NAFLD, followed by the step of administering to a subject in need of such treatment a pharmaceutical composition described herein, thereby treating or reducing the incidence of NAFLD in a human.

In certain embodiments, the treated disorder is selected from the group consisting of bland steatosis, non-alcoholic steatohepatitis (NASH), and lobular necroinflammation with fibrosis.

In other embodiments, the disorder is bland steatosis; in other embodiments, it is non-alcoholic steatohepatitis (NASH); and in still other embodiments, it is lobular necroinflammation with fibrosis.

Those skilled in the art will appreciate in light of the present disclosure that NAFLD and sequelae thereof may be present in subjects with diabetes, subjects exhibiting insulin resistance who do not have frank diabetes, and subjects that do not exhibit insulin resistance. In some embodiments, the subject treated by the described methods and compositions exhibits insulin resistance but does not have frank diabetes. In other embodiments, the subject does not exhibit insulin resistance. In other embodiments, the subject is obese but has well-controlled plasma glucose levels. In other embodiments, the treated subject is non-obese (Younossi et al 2012).

Methods of diagnosing and measuring non-alcoholic steatohepatitis are well known in the art, and include, for example, ultrasound, for example hepatorenal echo contrast, liver brightness, and vascular blurring under abdominal ultrasonography (Saverymuttu et al); measurement of liver enzyme levels, e.g. aspartate transaminase (AST), alanine transaminase (ALT), alkaline phosphatase, and gamma-glutamyl transpeptidase (GGT); hepatic mRNA levels of genes involved in lipogenesis; and hepatic diacylglycerol acyltransferase-2 (DGAT2) levels (Miyashita T et al 2012; Sung et al 2012; and Juurinen et al 2007); magnetic resonance imaging (Mazhar et al, 2009); and measuring adiponectin levels.

It will be appreciated by those skilled in the art that various disorders disclosed herein are sequelae of NAFLD (see, for example, Sung et al, 2012; Chatrath et al 2012; Nseir et al, 2011; Salcedo et al, 2012). In other cases, as will also be appreciated by those skilled in the art, GLP-1 can have a therapeutic effect independently of its effects on NAFLD.

Provided herein, in another embodiment, is a pharmaceutical composition for treating, or in another aspect reducing the incidence of, elevated total cholesterol in a human with hepatic steatosis, said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In yet another embodiment, the pharmaceutical composition comprises insulin, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

In yet another aspect, a use of a combination of ingredients described herein is provided in the preparation of a medicament for treating, or in another aspect reducing the incidence of, elevated total cholesterol in a human with hepatic steatosis.

Still another aspect provides a method of treating, or in another aspect reducing the incidence of, elevated total cholesterol in a subject with hepatic steatosis, the method comprising the step of administering to a subject with hepatic steatosis a pharmaceutical composition described hereinabove, thereby treating or reducing the incidence of elevated total cholesterol.

Provided herein, in another embodiment, is a pharmaceutical composition for treating, or in another aspect reducing the incidence of, hypertriglyceridemia in a human with hepatic steatosis, said pharmaceutical composition comprising an insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In yet another embodiment, the pharmaceutical composition comprises insulin, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

In yet another aspect, a use of a combination of ingredients described herein is provided in the preparation of a medicament for treating, or in another aspect reducing the incidence of, hypertriglyceridemia in a human with hepatic steatosis.

Still another aspect provides a method of treating, or in another aspect reducing the incidence of, hypertriglyceridemia in a subject with hepatic steatosis, the method comprising the step of administering to a subject with hepatic steatosis a pharmaceutical composition described hereinabove, thereby treating or reducing the incidence of hypertriglyceridemia.

Provided herein, in another embodiment, is a pharmaceutical composition for treating, or in another aspect reducing the incidence of, an elevated serum apolipoprotein B (ApoB) level in a human with hepatic steatosis, said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In yet another embodiment, the pharmaceutical composition comprises insulin, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

In yet another aspect, a use of a combination of ingredients described herein is provided in the preparation of a medicament for treating, or in another aspect reducing the incidence of, an elevated serum ApoB level in a human with hepatic steatosis.

Still another aspect provides a method of treating, or in another aspect reducing the incidence of, an elevated serum ApoB level in a subject with hepatic steatosis, the method comprising the step of administering to a subject with hepatic steatosis a pharmaceutical composition described hereinabove, thereby treating or reducing the incidence of elevated serum ApoB.

Provided herein, in another embodiment, is a pharmaceutical composition for treating, or in another aspect reducing the incidence of, an elevated total cholesterol/HDL ratio in a human with hepatic steatosis, said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In yet another embodiment, the pharmaceutical composition comprises insulin, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

In yet another aspect, a use of a combination of ingredients described herein is provided in the preparation of a medicament for treating, or in another aspect reducing the incidence of, an elevated total cholesterol/HDL ratio in a human with hepatic steatosis.

Still another aspect provides a method of treating, or in another aspect reducing the incidence of, an elevated total cholesterol/HDL ratio in a subject with hepatic steatosis, the method comprising the step of administering to a subject with hepatic steatosis a pharmaceutical composition described hereinabove, thereby treating or reducing the incidence of an elevated total cholesterol/HDL ratio.

Provided herein, in another embodiment, is a pharmaceutical composition for treating, or in another aspect reducing the incidence of, an elevated apolipoprotein B (ApoB)/ apolipoprotein A1 (ApoA1) ratio in a human with hepatic steatosis, said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In yet another embodiment, the pharmaceutical composition comprises insulin, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

In yet another aspect, a use of a combination of ingredients described herein is provided in the preparation of a medicament for treating, or in another aspect reducing the incidence of, an elevated ApoB/ApoA1 ratio in a human with hepatic steatosis.

Still another aspect provides a method of treating, or in another aspect reducing the incidence of, an elevated ApoB/ApoA1 ratio in a subject with hepatic steatosis, the method comprising the step of administering to a subject with hepatic steatosis a pharmaceutical composition described hereinabove, thereby treating or reducing the incidence of an elevated ApoB/ApoA1 ratio.

Methods for measuring each of the aforementioned lipid parameters are well known to those skilled in the art. Exemplary methods are described inter alia in Chiquette E et al and Martinez-Colubi M et al.

Provided herein, in another embodiment, is a pharmaceutical composition for treating, or in another aspect reducing the incidence of, an impaired insulin-induced enhancement of vasodilator response in a subject, said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In yet another embodiment, the pharmaceutical composition comprises insulin, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

In yet another aspect, a use of a combination of ingredients described herein is provided in the preparation of a medicament for treating, or in another aspect reducing the incidence of, an impaired insulin-induced enhancement of vasodilator response in a subject.

Still another aspect provides a method of treating, or in another aspect reducing the incidence of, an impaired insulin-induced enhancement of vasodilator response in a subject, the method comprising the step of administering to a subject a pharmaceutical composition described hereinabove, thereby treating or reducing the incidence of an impaired insulin-induced enhancement of vasodilator response.

Another aspect provides a method of treating an impaired insulin-induced enhancement of vasodilator responses in a subject with NAFLD, the method comprising the step of administering to a subject in need of such treatment a pharmaceutical composition described hereinabove, thereby treating an impaired insulin-induced enhancement of vasodilator responses in a subject with NAFLD. Methods for measuring insulin-induced vasodilator responses are known in the art, and include, for example, measuring blood flow responses (for example in the forearm) to acetylcholine (ACh) and sodium nitroprusside (SNP) (Tesauro et al).

Provided herein, in another embodiment, is a pharmaceutical composition for reducing, or in another aspect reducing the incidence of, fat deposition in the liver, said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In yet another embodiment, the pharmaceutical composition comprises insulin, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

In yet another aspect, a use of a combination of ingredients described herein is provided in the preparation of a medicament for reducing, or in another aspect reducing the incidence of, fat deposition in the liver.

Still another aspect provides a method of reducing, or in another aspect reducing the incidence of, fat deposition in the liver, the method comprising the step of administering to a subject a pharmaceutical composition described hereinabove, thereby reducing or reducing the incidence of fat deposition in the liver.

Provided herein, in another embodiment, is a pharmaceutical composition for preventing or reducing the incidence of a cardioembolism, said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In yet another embodiment, the pharmaceutical composition comprises insulin, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

In yet another aspect, a use of a combination of ingredients described herein is provided in the preparation of a medicament for preventing or reducing the incidence of a cardioembolism.

Still another aspect provides a method of preventing or reducing the incidence of a cardioembolism, the method comprising the step of administering to a subject a pharmaceutical composition described hereinabove, thereby preventing or reducing the incidence of a cardioembolism.

Provided herein, in another embodiment, is a pharmaceutical composition for reversing, or in another aspect reducing the incidence of, endothelial dysfunction, said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In yet another embodiment, the pharmaceutical composition comprises insulin, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

In yet another aspect, a use of a combination of ingredients described herein is provided in the preparation of a medicament for reversing, or in another aspect reducing the incidence of, endothelial dysfunction.

Still another aspect provides a method of reversing, or in another aspect reducing the incidence of, endothelial dysfunction, the method comprising the step of administering to a subject a pharmaceutical composition described hereinabove, thereby reversing or reducing the incidence of endothelial dysfunction.

Provided herein, in another embodiment, is a pharmaceutical composition for reversing, or in another aspect reducing the incidence of, a condition selected from a prothrombotic state and a state of platelet activation, said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In yet another embodiment, the pharmaceutical composition comprises insulin, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

In yet another aspect, a use of a combination of ingredients described herein is provided in the preparation of a medicament for reversing, or in another aspect reducing the incidence of, a condition selected from a prothrombotic state and a state of platelet activation.

Still another aspect provides a method of reversing, or in another aspect reducing the incidence of, a condition selected from a prothrombotic state and a state of platelet activation, the method comprising the step of administering to a subject a pharmaceutical composition described hereinabove, thereby reversing or reducing the incidence of a condition selected from a prothrombotic state and a state of platelet activation.

Provided herein, in another embodiment, is a pharmaceutical composition for reversing, or in another aspect reducing the incidence of, sub-clinical systemic inflammation, said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In yet another embodiment, the pharmaceutical composition comprises insulin, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

In yet another aspect, a use of a combination of ingredients described herein is provided in the preparation of a medicament for reversing, or in another aspect reducing the incidence of, sub-clinical systemic inflammation.

Still another aspect provides a method of reversing, or in another aspect reducing the incidence of, sub-clinical systemic inflammation, the method comprising the step of administering to a subject a pharmaceutical composition described hereinabove, thereby reversing or reducing the incidence of sub-clinical systemic inflammation.

Provided herein, in another embodiment, is a pharmaceutical composition for reducing the incidence of, or in another aspect reversing, atherosclerosis, said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In yet another embodiment, the pharmaceutical composition comprises insulin, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

In yet another aspect, a use of a combination of ingredients described herein is provided in the preparation of a medicament for reducing the incidence of, or in another aspect reversing, atherosclerosis.

Still another aspect provides a method of reducing the incidence of, or in another aspect reversing, atherosclerosis, the method comprising the step of administering to a subject a pharmaceutical composition described hereinabove, thereby reducing the incidence of or reversing atherosclerosis.

Provided herein, in another embodiment, is a pharmaceutical composition for reducing the incidence of, or in another aspect preventing, obesity, which is in one embodiment central obesity, said pharmaceutical composition comprising said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In yet another embodiment, the pharmaceutical composition comprises insulin, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

In yet another aspect, a use of a combination of ingredients described herein is provided in the preparation of a medicament for reducing the incidence of, or in another aspect preventing, obesity.

Still another aspect provides a method of reducing obesity in a subject with hepatic steatosis, the method comprising the step of administering to a subject with hepatic steatosis a pharmaceutical composition described hereinabove, thereby reducing obesity.

Provided herein, in another embodiment, is a pharmaceutical composition for reducing hepatic insulin resistance in a subject with hepatic steatosis, said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In yet another embodiment, the pharmaceutical composition comprises insulin, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

In yet another aspect, a use of a combination of ingredients described herein is provided in the preparation of a medicament for reducing hepatic insulin resistance in a subject with hepatic steatosis.

Still another aspect provides a method of reducing hepatic insulin resistance in a subject with hepatic steatosis, the method comprising the step of administering to a subject with hepatic steatosis a pharmaceutical composition described hereinabove, thereby reducing hepatic insulin resistance in a subject with hepatic steatosis.

The oil, insulin, GLP-1 analogue, protease inhibitor(s), chelator, coating, and other optional ingredients of the described methods and compositions may be any of those described herein; each alternative may be combined freely to form discrete embodiments of the invention disclosed herein.

"Liquid" as used herein refers to a phase that flows freely and has a constant volume under ambient conditions. Fish oil, for instance, is a liquid under ambient conditions. The term includes oil-based solutions, suspensions, and combinations thereof. In alternative embodiments, the term may refer to a composition that has a viscosity within the range of 1-1000 millipascal seconds, inclusive, at 20° C.

In embodiments where both a GLP-1 analogue and insulin are both present, these two components are indicated for co-administration together, either in the same or in separate dosage forms. In the case of separate dosage forms, "co-administration" in this regard, may refer either to simultaneous administration or, in another embodiment, to administration within 30 minutes of each other. In still other embodiments, the different components are indicated for administration in a particular order, separated by a set time interval that will typically be 30 minutes or less. For example, the insulin-containing dosage form may be indicated for administration 2-10 minutes after the exenatide-containing dosage form; in other embodiments, 10-20 minutes after the exenatide-containing dosage form; in other embodiments, 20-30 minutes after the exenatide-containing dosage form; and in other embodiments, 30-60 minutes after the exenatide-containing dosage form. Oral dosage forms such as those provided herein lend themselves to sequential administration more than injected dosage forms, since regimens requiring repeated injections are likely to be associated with low rates of compliance.

Reference herein to "extended" administration may refer, in various embodiments, to administration for more than 1 month, more than 6 weeks, more than 2 months, more than 3 months, more than 4 months, more than 5 months, more than 6 months, more than 7 months, more than 8 months, more than 9 months, more than 10 months, more than 12 months, more than 15 months, more than 18 months, more than 24 months, more than 30 months, or more than 36 months, more than 48 months, more than 60 months, more than 72 months, more than 96 months, more than 10 years, more than 15 years, or more than 20 years. In other embodiments, the term may refer to administration for 1-60 months, 2-60 months, 3-60 months, 4-60 months, 5-60 months, 6-60 months, 8-60 months, 10-60 months, 12-60 months, 1-36 months, 2-36 months, 3-36 months, 4-36 months, 5-36 months, 6-36 months, 8-36 months, 10-36 months, 12-36 months, 1-36 months, 2-24 months, 3-24 months, 4-24 months, 5-24 months, 6-24 months, 8-24 months, 10-24 months, 12-24 months, 1-120 months, 2-120 months, 3-120 months, 4-120 months, 5-120 months, 6-120 months, 8-120 months, 10-120 months, 12-120 months, 1-240 months, 2-240 months, 3-240 months, 4-240 months, 5-240 months, 6-240 months, 8-240 months, 10-240 months, or 12-240 months.

In more specific embodiments, between 8-16 mg of insulin is administered once per day for more than 1 month, more than 6 weeks, more than 2 months, more than 3 months, more than 4 months, more than 5 months, more than 6 months, more than 7 months, more than 8 months, more than 9 months, more than 10 months, more than 12 months, more than 15 months, more than 18 months, more than 24 months, more than 30 months, or more than 36 months, more than 48 months, more than 60 months, more than 72 months, more than 96 months, more than 10 years, more than 15 years, or more than 20 years. In other embodiments, the term may refer to administration for 1-60 months, 2-60 months, 3-60 months, 4-60 months, 5-60 months, 6-60 months, 8-60 months, 10-60 months, 12-60 months, 1-36 months, 2-36 months, 3-36 months, 4-36 months, 5-36 months, 6-36 months, 8-36 months, 10-36 months, 12-36 months, 1-36 months, 2-24 months, 3-24 months, 4-24 months, 5-24 months, 6-24 months, 8-24 months, 10-24 months, 12-24 months, 1-120 months, 2-120 months, 3-120 months, 4-120 months, 5-120 months, 6-120 months, 8-120 months, 10-120 months, 12-120 months, 1-240 months, 2-240 months, 3-240 months, 4-240 months, 5-240 months, 6-240 months, 8-240 months, 10-240 months, or 12-240 months.

In still other embodiments, between 8-16 mg of insulin is administered twice per day for more than 1 month, more than 6 weeks, more than 2 months, more than 3 months, more than 4 months, more than 5 months, more than 6 months, more than 7 months, more than 8 months, more than 9 months, more than 10 months, more than 12 months, more than 15 months, more than 18 months, more than 24 months, more than 30 months, or more than 36 months, more than 48 months, more than 60 months, more than 72 months, more than 96 months, more than 10 years, more than 15 years, or more than 20 years. In other embodiments, the term may refer to administration for 1-60 months, 2-60 months, 3-60 months, 4-60 months, 5-60 months, 6-60 months, 8-60 months, 10-60 months, 12-60 months, 1-36 months, 2-36 months, 3-36 months, 4-36 months, 5-36 months, 6-36 months, 8-36 months, 10-36 months, 12-36 months, 1-36 months, 2-24 months, 3-24 months, 4-24 months, 5-24 months, 6-24 months, 8-24 months, 10-24 months, 12-24 months, 1-120 months, 2-120 months, 3-120 months, 4-120 months, 5-120 months, 6-120 months, 8-120 months, 10-120 months, 12-120 months, 1-240 months, 2-240 months, 3-240 months, 4-240 months, 5-240 months, 6-240 months, 8-240 months, 10-240 months, or 12-240 months.

In yet other embodiments, between 300-600 mcg of exenatide is administered once per day, for more than 1 month, more than 6 weeks, more than 2 months, more than 3 months, more than 4 months, more than 5 months, more than 6 months, more than 7 months, more than 8 months, more than 9 months, more than 10 months, more than 12 months, more than 15 months, more than 18 months, more than 24 months, more than 30 months, or more than 36 months, more than 48 months, more than 60 months, more than 72 months, more than 96 months, more than 10 years, more than 15 years, or more than 20 years. In other embodiments, the term may refer to administration for 1-60 months, 2-60 months, 3-60 months, 4-60 months, 5-60 months, 6-60 months, 8-60 months, 10-60 months, 12-60 months, 1-36 months, 2-36 months, 3-36 months, 4-36 months, 5-36 months, 6-36 months, 8-36 months, 10-36 months, 12-36 months, 1-36 months, 2-24 months, 3-24 months, 4-24 months, 5-24 months, 6-24 months, 8-24 months, 10-24 months, 12-24 months, 1-120 months, 2-120 months, 3-120 months, 4-120 months, 5-120 months, 6-120 months, 8-120 months, 10-120 months, 12-120 months, 1-240 months, 2-240 months, 3-240 months, 4-240 months, 5-240 months, 6-240 months, 8-240 months, 10-240 months, or 12-240 months.

In yet other embodiments, between 300-600 mcg of exenatide is administered twice per day, for more than 1 month, more than 6 weeks, more than 2 months, more than 3 months, more than 4 months, more than 5 months, more than 6 months, more than 7 months, more than 8 months, more than 9 months, more than 10 months, more than 12 months, more than 15 months, more than 18 months, more than 24 months, more than 30 months, or more than 36 months, more than 48 months, more than 60 months, more than 72 months, more than 96 months, more than 10 years, more than 15 years, or more than 20 years. In other embodiments, the tom may refer to administration for 1-60 months, 2-60 months, 3-60 months, 4-60 months, 5-60 months, 6-60 months, 8-60 months, 10-60 months, 12-60 months, 1-36 months, 2-36 months, 3-36 months, 4-36 months, 5-36 months, 6-36 months, 8-36 months, 10-36 months, 12-36 months, 1-36 months, 2-24 months, 3-24 months, 4-24 months, 5-24 months, 6-24 months, 8-24 months, 10-24 months, 12-24 months, 1-120 months, 2-120 months, 3-120 months, 4-120 months, 5-120 months, 6-120 months, 8-120 months, 10-120 months, 12-120 months, 1-240 months, 2-240 months, 3-240 months, 4-240 months, 5-240 months, 6-240 months, 8-240 months, 10-240 months, or 12-240 months.

In yet other embodiments, between 300-600 mcg of exenatide is administered three times per day, or in other embodiments up to 3 times per day, for more than 1 month, more than 6 weeks, more than 2 months, more than 3 months, more than 4 months, more than 5 months, more than 6 months, more than 7 months, more than 8 months, more than 9 months, more than 10 months, more than 12 months, more than 15 months, more than 18 months, more than 24 months, more than 30 months, or more than 36 months, more than 48 months, more than 60 months, more than 72 months, more than 96 months, more than 10 years, more than 15 years, or more than 20 years. In other embodiments, the term may refer to administration for 1-60 months, 2-60 months, 3-60 months, 4-60 months, 5-60 months, 6-60 months, 8-60 months, 10-60 months, 12-60 months, 1-36 months, 2-36 months, 3-36 months, 4-36 months, 5-36 months, 6-36 months, 8-36 months, 10-36 months, 12-36 months, 1-36 months, 2-24 months, 3-24 months, 4-24 months, 5-24 months, 6-24 months, 8-24 months, 10-24 months, 12-24 months, 1-120 months, 2-120 months, 3-120 months, 4-120 months, 5-120 months, 6-120 months, 8-120 months, 10-120 months, 12-120 months, 1-240 months, 2-240 months, 3-240 months, 4-240 months, 5-240 months, 6-240 months, 8-240 months, 10-240 months, or 12-240 months.

Once-per-day administration, as used herein, can refer to administration during any time of day, or in other embodiments, administration each day at a specific time of day. In certain embodiments, once per day administration may be before bedtime.

Insulin Proteins and GLP-1 Analogues

Insulin proteins and GLP-1 analogues for use as described herein are in some embodiments isolated prior to their introduction into the described pharmaceutical compositions. "Isolated" in this regard excludes provision of the insulin and/or GLP-1 analogue as a homogenized tissue preparation or other form containing substantial amounts of contaminating proteins. An example of an isolated protein or peptide is a recombinant protein or peptide. An alternative embodiment is a synthetic protein or peptide.

A person skilled in the art will appreciate in light of the present disclosure that various types of insulin are suitable for the described methods and compositions. Exemplary insulin proteins include but are not limited to both wild-type and mutated insulin proteins, including synthetic human insulin, synthetic bovine insulin, synthetic porcine insulin, synthetic whale insulin, and metal complexes of insulin, such as zinc complexes of insulin, protamine zinc insulin, and globin zinc.

Various classes of insulin may also be utilized, for example fast-acting insulin, lente insulin, semilente insulin, ultralente insulin, NPH insulin, glargine insulin, lispro insulin, aspart insulin, or combinations of two or more of the above types of insulin.

In certain embodiments, the insulin of the described methods and compositions is wild-type human insulin (Uniprot ID P01308). In some embodiments, human insulin is produced as a recombinant protein in bacterial cells. In other embodiments, human insulin is produced synthetically.

GLP-1 analogues are also referred to in the art as GLP-1 mimetics. A person of skill in the art will appreciate that the described compositions may include at least one of the following GLP-1 analogues: exenatide (Byetta™; CAS no. 141732-76-5; SEQ ID NO: 4), lixisenatide (CAS no. 320367-13-3), liraglutide (CAS no. 204656-20-2), exendin-9 (CAS no. 133514-43-9), AC3174 ([Leu(14)]exendin-4, Amylin Pharmaceuticals, Inc.), taspoglutide (CAS no. 275371-94-3), albiglutide (CAS no. 782500-75-8), semaglutide (CAS no. 910463-68-2), LY2189265 (Dulaglutide™; CAS no. 923950-08-7), and CJC-1134-PC (a modified Exendin-4 analogue conjugated to recombinant human albumin manufactured by ConjuChem™). All CAS records were accessed on Dec. 19, 2011. Thus, in certain embodiments, the described method or composition utilizes any of the above-listed GLP-1 analogues. In other embodiments, one of the above-listed GLP-1 analogues is selected. Those of skill in the art will appreciate in light of the findings of described herein that other GLP-1 analogues can also be utilized.

Therapeutic insulin and GLP-1 proteins suitable for use in the present invention include derivatives that are modified (i.e., by the covalent attachment of a non-amino acid residue to the protein). For example, but not by way of limitation, the protein includes proteins that have been modified, e.g., by glycosylation, acetylation, PEGylation, phosphorylation, amidation, or derivatization by known protecting/blocking groups. High-MW PEG can be attached to therapeutic proteins with or without a multifunctional linker either through site-specific conjugation of the PEG to the N- or C-terminus thereof or via epsilon-amino groups present on lysine residues. Additionally, the derivative may contain one or more non-classical amino acids, for example D-isomers of the common amino acids, 2,4-diaminobutyric acid, α-amino isobutyric acid, A-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, and Nα-methyl amino acids.

Emulsifiers

In certain embodiments, an oil-based liquid formulation utilized in the described methods and pharmaceutical compositions further comprises an emulsifier. Those skilled in the art will recognize, in light of the present disclosure, that a variety of pharmaceutically compatible emulsifiers can be utilized.

In certain embodiments, the emulsifier is a component provided as a mixture of (a) a monoacylglycerol (monoglyceride), a diacylglycerol (diglyceride), a triacylglycerol (triglyceride), or a mixture thereof; and (b) a polyethylene glycol (PEG) ester of a fatty acid. In this regard, each of the terms "monoacylglycerol", "diacylglycerol", and "triacylglycerol" need not refer to a single compound, but rather can include mixtures of compounds, for example mixtures of monoacylglycerols, diacylglycerols, or triacylglycerols having fatty acids of varying lengths. In certain preferred embodiments, monoacylglycerols, diacylglycerols, or triacylglycerols utilized in the described methods and compositions, for example those used to general PEG esters, are from an oil source that is Generally Recognized As Safe (GRAS). Examples of GRAS oil sources are coconut oil, corn oil, peanut oil, soybean oil, Myvacet 9-45 (Diacetylated monoglycerides of C-18 fatty acids).

More specific lengths of PEG moieties for use in some embodiments of the described compositions and methods contain between 5-100 monomers. In more specific embodiments, the PEG may contain between 15-50 monomers. In still more specific embodiments, the PEG may contain between 25-40 monomers. In more specific embodiments, the PEG may contain 32 monomers.

Examples of components meeting the above specifications are Gelucire™ 44/14, Gelucire™ 53/10, and Gelucire™ 50/13. A more specific example is Gelucire™ 44/14. The suffixes 44 and 14 refer respectively to its melting point and its hydrophilic/lypophilic balance (HLB). Gelucire™ 44/14 (Gattefossé SAS, Saint-Priest, France) is obtained by polyglycolysis of hydrogenated coconut oil (medium and long chain triacylglycerols with PEG-32. It has a hydrophile/lipophile balance of 14. It is composed of a defined admixture of $C_8$-$C_{18}$ mono-, di- and triacylglycerols (20% w/w); PEG-32 mono- and diesters and free PEG-32 (80% w/w). The main fatty acid present is lauric acid, accounting for 45% on average of the total fatty acid content. It is a solid dispersion composed of a PEG ester fraction under a lamellar phase of 120 Å with a helical conformation and an acylglycerol fraction under a hexagonal packing. The main products of simulated gastrointestinal lipolysis of Gelucire™ 44/14 are PEG-32 mono and diesters.

In some embodiments, the HLB of a self-emulsifying component utilized in the described methods and compositions is 10 or greater. In other embodiments, it is between 11-19. In other embodiments, it is between 12-18. In other embodiments, it is between 12-17. In other embodiments, it is between 12-16 inclusive, which is indicative of an oil-in-water (O/W) emulsifier. In other embodiments, it is between 13-15. In other embodiments, it is 14. Still more specific embodiments of self-emulsifying components have an HLB of 12-16 inclusive and comprise medium- and long-chain triacylglycerols conjugated to PEG, free triacylglycerols, and free PEG. In other embodiments, the self-emulsifying component has an HLB of 12-16 inclusive and consists of a mixture of medium- and long-chain triacylglycerols conjugated to PEG, free triacylglycerols, and free PEG. In other embodiments, the self-emulsifying component has an HLB of 14 and comprises medium- and long-chain triacylglycerols conjugated to PEG, free triacylglycerols, and free PEG. In other embodiments, the self-emulsifying component has an HLB of 14 and consists of a mixture of medium- and long-chain triacylglycerols conjugated to PEG, free triacylglycerols, and free PEG.

In certain embodiments, the aforementioned emulsifier, which is in certain embodiments a self-emulsifying component, constitutes 8-16% weight/weight inclusive of the oil-based liquid formulation. In more specific embodiments, the amount is 9-15% inclusive. In more specific embodiments, the amount is 10-14% inclusive. In more specific embodiments, the amount is 11-13% inclusive. In more specific embodiments, the amount is 12%.

Non-Ionic Detergents

In certain embodiments, the oil-based liquid formulation utilized in the described methods and pharmaceutical compositions further comprises a polysorbate-based detergent. Examples of polysorbate-based detergent are detergents derived by covalently bonding polyethoxylated sorbitan to a fatty acid. More specific embodiments of polysorbate-based detergents are polysorbate-20, polysorbate-40, and polysorbate-80.

For example, polysorbate 80 (Tween-80) is a mild, non-ionic detergent derived from polyethoxylated sorbitan and oleic acid and having the following structure:

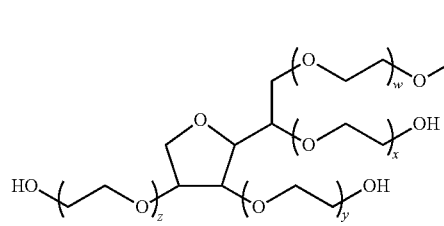
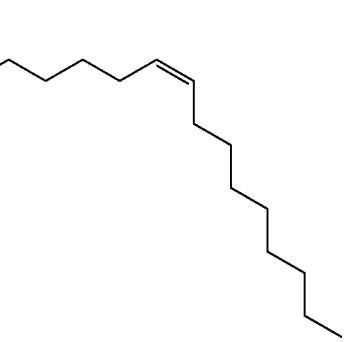

w + x + y + z = 20

In the case of polysorbate 80, the moiety shown on the right side is a mixture of fatty acids, containing 60-70% oleic acid (as depicted), with the balance being primarily linoleic, palmitic, and stearic acids.

In a more specific embodiment, the polysorbate 80 constitutes 3-10% weight/weight inclusive of an oil-based liquid formulation used in the described methods and compositions. In a more specific embodiment, the percentage is 4-8% inclusive. In a more specific embodiment, the percentage is 4.5-6% inclusive. In a more specific embodiment, the percentage is 5%.

Dosages

In more specific embodiments, the amount of insulin in a dosage form of the described methods and compositions is between 6-64 mg. In other embodiments, the amount is between 6-56 mg. In other embodiments, the amount is between 6-48 mg. In other embodiments, the amount is between 6-40 mg. In other embodiments, the amount is between 6-36 mg. In other embodiments, the amount is between 6-32 mg. In other embodiments, the amount is between 6-28 mg. In other embodiments, the amount is between 6-24 mg. In other embodiments, the amount is between 6-20 mg. In other embodiments, the amount is between 6-14 mg. In other embodiments, the amount is between 6-12 mg. In other embodiments, the amount is between 6-10 mg. In other embodiments, the amount is between 10-64 mg. In other embodiments, the amount is between 10-56 mg. In other embodiments, the amount is between 10-48 mg. In other embodiments, the amount is between 10-40 mg. In other embodiments, the amount is between 10-36 mg. In other embodiments, the amount is between 10-32 mg. In other embodiments, the amount is between 10-28 mg. In other embodiments, the amount is between 16-64 mg. In other embodiments, the amount is between 16-56 mg. In other embodiments, the amount is between 16-48 mg. In other embodiments, the amount is between 16-40 mg. In other embodiments, the amount is between 16-36 mg. In other embodiments, the amount is between 16-32 mg. In other embodiments, the amount is between 16-28 mg. In certain embodiments, the above dosage amounts are a daily dose.

In other embodiments, the amount is 8 mg. In other embodiments, the amount is 12 mg. In other embodiments, the amount is 16 mg. In other embodiments, the amount is 20 mg. In other embodiments, the amount is 24 mg. In other embodiments, the amount is 32 mg. In other embodiments, the amount is 40 mg. In other embodiments, the amount is 40 mg. In other embodiments, the amount is 56 mg. In other embodiments, the amount is 64 mg. In other embodiments, the amount is between 8-16 mg. In other embodiments, the amount is between 8-14 mg. In other embodiments, the amount is between 8-12 mg. In other embodiments, the amount is between 8-10 mg. In other embodiments, the amount is 16 mg. In other embodiments, the amount is between 10-16 mg. In other embodiments, the amount is between 10-14 mg. In other embodiments, the amount is between 10-18 mg. In certain embodiments, the above dosage amounts are a daily dose.

In other embodiments, the amount of insulin in a dosage form of the described methods and compositions is between 0.06-0.64 mg/kg (milligrams per kilogram body weight). In other embodiments, the amount is between 0.06-0.56 mg/kg. In other embodiments, the amount is between 0.06-0.48 mg/kg. In other embodiments, the amount is between 0.06-0.40 mg/kg. In other embodiments, the amount is between 0.06-0.32 mg/kg. In other embodiments, the amount is between 0.06-0.28 mg/kg. In other embodiments, the amount is between 0.06-0.24 mg/kg. In other embodiments, the amount is between 0.06-0.20 mg/kg. In other embodiments, the amount is between 0.10-0.16 mg/kg. In other embodiments, the amount is between 0.10-0.64 mg/kg. In other embodiments, the amount is between 0.10-0.56 mg/kg. In other embodiments, the amount is between 0.10-0.48 mg/kg. In other embodiments, the amount is between 0.10-0.40 mg/kg. In other embodiments, the amount is between 0.10-0.32 mg/kg. In other embodiments, the amount is between 0.10-0.28 mg/kg. In other embodiments, the amount is between 0.10-0.24 mg/kg. In other embodiments, the amount is between 0.10-0.20 mg/kg. In other embodiments, the amount is between 0.06-0.14 mg/kg. In other embodiments, the amount is between 0.06-0.12 mg/kg. In other embodiments, the amount is between 0.06-0.10 mg/kg. In other embodiments, the amount is 0.08 mg/kg. In other embodiments, the amount is 0.12 mg/kg. In other embodiments, the amount is 0.16 mg/kg. In other embodiments, the amount is between 0.08-0.16 mg/kg. In other embodiments, the amount is between 0.08-0.14 mg/kg. In other embodiments, the amount is between 0.08-0.12 mg/kg. In other embodiments, the amount is between 0.08-0.10 mg/kg. In other embodiments, the amount is between 0.10-0.16 mg/kg. In other embodiments, the amount is between 0.10-0.18 mg/kg. In other embodiments, the amount is between 0.10-0.14 mg/kg. In certain embodiments, the above dosage amounts are a daily dose.

In still other embodiments, the amount of insulin in the dosage form is an amount corresponding to one of the above amounts or ranges for an adult, adjusted per body weight for a pediatric patient. Adjustments of this kind mentioned herein utilize 62 kilograms as the adult weight. In other embodiments, the insulin is present in an amount adjusted for a pediatric patient, and the GLP-1 analogue is also present in an amount adjusted for a pediatric patient. In certain embodiments, the above dosage amounts are a daily dose. In one embodiment, insulin is present in the pharmaceutical composition in an amount between 8-32 mg (inclusive) per dose for an adult patient or a corresponding amount per body weight for a pediatric patient.

The dosages described herein for insulin may be for wild-type human insulin, or in another embodiment, for one of the other types of insulin known in the art.

In other embodiments, the amount of a GLP-1 analogue in a dosage form of the described methods and compositions is 150 micrograms (mcg), 200 mcg, 250 mcg, 300 mcg, 350 mcg, 400 mcg, 500 mcg, or 600 mcg. In other embodiments, the amount of GLP-1 analogue is between 100-1600 mcg inclusive for an adult patent. In other embodiments, the amount is between 100-1400 mcg. In other embodiments, the amount is between 100-1200 mcg. In other embodiments, the amount is between 100-1000 mcg. In other embodiments, the amount is between 100-800 mcg. In other embodiments, the amount is between 100-700 mcg. In other embodiments, the amount is between 100-600 mcg. In other embodiments, the amount is between 100-500 mcg. In other embodiments, the amount is between 100-400 mcg. In other embodiments, the amount is between 200-1400 mcg. In other embodiments, the amount is between 200-1400 mcg. In other embodiments, the amount is between 200-1200 mcg. In other embodiments, the amount is between 200-1000 mcg. In other embodiments, the amount is between 200-800 mcg. In other embodiments, the amount is between 200-700 meg. In other embodiments, the amount is between 200-600 mcg. In other embodiments, the amount is between 200-500 mcg. In other embodiments, the amount is between 200-400 mcg. In other embodiments, the amount is between 100-300 mcg. In other embodiments, the amount is between 100-250 mcg. In other embodiments, the amount is between 100-200 mcg. In other embodiments, the amount is between 100-150 mcg. In other embodiments, the amount is 100 mcg. In other embodiments, the amount is 150 mcg. In other embodiments, the amount is 200 meg. In other embodiments, the amount is 250 meg. In other embodiments, the amount is 300 mcg. In other embodiments, the amount is between 150-400 mcg. In other embodiments, the amount is between 150-300 mcg. In other embodiments, the amount is between 150-250 meg. In other embodiments, the amount is between 150-200 mcg. In certain embodiments, the above dosage amounts are a daily dose. In still other embodiments, the GLP-1 analogue is exenatide, present in one of the above amounts.

In other embodiments, the amount of GLP-1 analogue in a dosage form of the described methods and compositions is between 0.100-1.60 mcg/kg for an adult patent. In other embodiments, the amount is between 0.100-1.40 meg/kg. In other embodiments, the amount is between 0.100-1.20 mcg/kg. In other embodiments, the amount is between 0.100-1.0 mcg/kg. In other embodiments, the amount is between 0.100-0.800 meg/kg. In other embodiments, the amount is between 0.100-0.700 meg/kg. In other embodiments, the amount is between 0.100-0.600 mcg/kg. In other embodiments, the amount is between 0.100-0.500 mcg/kg. In other embodiments, the amount is between 0.100-0.400 mcg/kg. In other embodiments, the amount is between 0.200-1.40 mcg/kg. In other embodiments, the amount is between 0.200-1.40 mcg/kg. In other embodiments, the amount is between 0.200-1.20 mcg/kg. In other embodiments, the amount is between 0.200-1.0 mcg/kg. In other embodiments, the amount is between 0.200-0.800 meg/kg. In other embodiments, the amount is between 0.200-0.700 mcg/kg. In other embodiments, the amount is between 0.200-0.600 mcg/kg. In other embodiments, the amount is between 0.200-0.500 mcg/kg. In other embodiments, the amount is between 0.200-0.400 mcg/kg. In other embodiments, the amount is between 0.100-0.300 mcg/kg. In other embodiments, the amount is between 0.100-0.250 meg/kg. In other embodiments, the amount is between 0.100-0.200 meg/kg. In other embodiments, the amount is between 0.100-0.150 mcg/kg. In other embodiments, the amount is 0.100 meg/kg. In other embodiments, the amount is 0.150 mcg/kg. In other embodiments, the amount is 0.200 mcg/kg. In other embodiments, the amount is 0.250 mcg/kg. In other embodiments, the amount is 0.300 mcg/kg. In other embodiments, the amount is between 0.150-0.400 mcg/kg. In other embodiments, the amount is between 0.150-0.300 meg/kg. In other embodiments, the amount is between 0.150-0.250 mcg/kg. In other embodiments, the amount is between 0.100-0.200 meg/kg. In certain embodiments, the above dosage amounts are a daily dose. In still other embodiments, the GLP-1 analogue is exenatide, present in one of the above amounts.

In other embodiments, the amount of GLP-1 analogue in the dosage form is an amount corresponding to one of the above amounts or ranges for an adult, adjusted per body weight for a pediatric patient. In other embodiments, the GLP-1 analogue is present in an amount adjusted for a pediatric patient, and the insulin is also present in an amount adjusted for a pediatric patient, for example an amount corresponding to 4-12 mg inclusive for an adult patent, adjusted for the weight of the a pediatric patient. In certain embodiments, the above dosage amounts are a daily dose. In still other embodiments, the GLP-1 analogue is exenatide, present in one of the above amounts.

In various embodiments, the described dosage form contains exenatide in an amount of between 100-600 mcg, 100-500 mcg, 100-400 mcg, 100-300 mcg, 200-600 mcg, 200-500 mcg, 200-400 mcg, 200-300 mcg, 150-300 mcg, or 150-250 mcg; together with 8-16 mg insulin. In other embodiments, the described dosage form contains exenatide in an amount of between 100-600 meg, 100-500 mcg, 100-400 mcg, 100-300 mcg, 200-600 mcg, 200-500 mcg, 200-400 mcg, 200-300 mcg, 150-300 mcg, or 150-250 mcg; together with 8-12 mg insulin. In other embodiments, the described dosage form contains exenatide in an amount of between 100-600 mcg, 100-500 mcg, 100-400 mcg, 100-300 mcg, 200-600 mcg, 200-500 mcg, 200-400 mcg, 200-300 mcg, 150-300 mcg, or 150-250 mcg; together with 12-16 mg insulin. In other embodiments, the described dosage form contains exenatide in an amount of between 100-600 mcg, 100-500 mcg, 100-400 mcg, 100-300 mcg, 200-600 mcg, 200-500 meg, 200-400 mcg, 200-300 mcg, 150-300 mcg, or 150-250 mcg; together with 16-24 mg insulin. In other embodiments, the described dosage form contains exenatide in an amount of between 100-600 mcg, 100-500 mcg, 100-400 mcg, 100-300 mcg, 200-600 mcg, 200-500 mcg, 200-400 mcg, 200-300 mcg, 150-300 mcg, or 150-250 mcg; together with 24-32 mg insulin. In other embodiments, the described dosage form contains exenatide in an amount of between 100-600 mcg, 100-500 mcg, 100-400 mcg, 100-300 mcg, 200-600 mcg, 200-500 mcg, 200-400 mcg, 200-300 mcg, 150-300 mcg, or 150-250 mcg; together with 12-16 mg insulin. In other embodiments, the described dosage form contains exenatide in an amount of between 100-600 mcg, 100-500 meg, 100-400 mcg, 100-300 mcg, 200-600 mcg, 200-500 mcg, 200-400 meg, 200-300 mcg, 150-300 mcg, or 150-250 mcg; together with 8 mg insulin. In other embodiments, the described dosage form contains exenatide in an amount of between 100-600 mcg, 100-500 mcg, 100-400 mcg, 100-300 mcg, 200-600 mcg, 200-500 mcg, 200-400 mcg, 200-300 mcg, 150-300 mcg, or 150-250 mcg; together with 12 mg insulin. In other embodiments, the described dosage form contains exenatide in an amount of between 100-600 mcg, 100-500 mcg, 100-400 mcg, 100-300 mcg, 200-600 mcg, 200-500 mcg, 200-400 mcg, 200-300 mcg, 150-300 mcg, or 150-250 mcg; together with 16 mg insulin. In other embodiments, the described dosage form contains exenatide in an amount of between 100-600 mcg, 100-500 mcg, 100-400 mcg, 100-300 mcg, 200-600 mcg, 200-500 mcg, 200-400 mcg, 200-300 mcg, 150-300 mcg, or 150-250 mcg; together with 20 mg insulin. In other embodiments, the described dosage form contains exenatide in an amount of between 100-600 mcg, 100-500 mcg, 100-400 mcg, 100-300 mcg, 200-600 mcg, 200-500 mcg, 200-400 mcg, 200-300 mcg, 150-300 mcg, or 150-250 mcg; together with 24 mg insulin. In other embodiments, the described dosage for n contains exenatide in an amount of between 100-600 mcg, 100-500 mcg, 100-400 mcg, 100-300 mcg, 200-600 mcg, 200-500 mcg, 200-400 mcg, 200-300 mcg, 150-300 mcg, or 150-250 mcg; together with 28 mg insulin. In other embodiments, the described dosage form contains exenatide in an amount of between 100-600 mcg, 100-500 mcg, 100-400 mcg, 100-300 mcg, 200-600 mcg, 200-500 mcg, 200-400 mcg, 200-300 mcg, 150-300 mcg, or 150-250 mcg; together with 32 mg insulin. In certain embodiments, the above dosage amounts are a daily dose.

In other embodiments, the described dosage form contains insulin in an amount of 8-32 mg, 8-28 mg, 8-24 mg, 8-20 mg, 8-16 mg, 8-12 mg, 12-32 mg, 16-32 mg, 20-32 mg, 24-32 mg, 12-24 mg, 16-24 mg, 12-20 mg, or 16-20 mg; together with 150-300 mcg exenatide. In other embodiments, the described dosage form contains insulin in an amount of 8-32 mg, 8-28 mg, 8-24 mg, 8-20 mg, 8-16 mg, 8-12 mg, 12-32 mg, 16-32 mg, 20-32 mg, 24-32 mg, 12-24 mg, 16-24 mg, 12-20 mg, or 16-20 mg; together with 300-450 mcg exenatide. In other embodiments, the described dosage form contains insulin in an amount of 8-32 mg, 8-28 mg, 8-24 mg, 8-20 mg, 8-16 mg, 8-12 mg, 12-32 mg, 16-32 mg, 20-32 mg, 24-32 mg, 12-24 mg, 16-24 mg, 12-20 mg, or 16-20 mg; together with 450-600 mcg exenatide. In other embodiments, the described dosage form contains insulin in an amount of 8-32 mg, 8-28 mg, 8-24 mg, 8-20 mg, 8-16 mg, 8-12 mg, 12-32 mg, 16-32 mg, 20-32 mg, 24-32 mg, 12-24 mg, 16-24 mg, 12-20 mg, or 16-20 mg; together with 100-150 mcg exenatide. In other embodiments, the described dosage form contains insulin in an amount of 8-32 mg, 8-28 mg, 8-24 mg, 8-20 mg, 8-16 mg, 8-12 mg, 12-32 mg, 16-32 mg, 20-32 mg, 24-32 mg, 12-24 mg, 16-24 mg, 12-20 mg, or 16-20 mg; together with 150-200 mcg exenatide. In other embodiments, the described dosage form contains insulin in an amount of 8-32 mg, 8-28 mg, 8-24 mg, 8-20 mg, 8-16 mg, 8-12 mg, 12-32 mg, 16-32 mg, 20-32 mg, 24-32 mg, 12-24 mg, 16-24 mg, 12-20 mg, or 16-20 mg; together with 200-250 mcg exenatide. In other embodiments, the described dosage form contains insulin in an amount of 8-32 mg, 8-28 mg, 8-24 mg, 8-20 mg, 8-16 mg, 8-12 mg, 12-32 mg, 16-32 mg, 20-32 mg, 24-32 mg, 12-24 mg, 16-24 mg, 12-20 mg, or 16-20 mg; together with 250-300 mcg exenatide. In certain embodiments, the above dosage amounts are a daily dose.

In other embodiments, the described dosage form contains insulin in an amount of 8-32 mg, 8-28 mg, 8-24 mg, 8-20 mg, 8-16 mg, 8-12 mg, 12-32 mg, 16-32 mg, 20-32 mg, 24-32 mg, 12-24 mg, 16-24 mg, 12-20 mg, or 16-20 mg; together with 100 mcg exenatide. In other embodiments, the described dosage form contains insulin in an amount of 8-32 mg, 8-28 mg, 8-24 mg, 8-20 mg, 8-16 mg, 8-12 mg, 12-32 mg, 16-32 mg, 20-32 mg, 24-32 mg, 12-24 mg, 16-24 mg, 12-20 mg, or 16-20 mg; together with 200 mcg exenatide. In other embodiments, the described dosage form contains insulin in an amount of 8-32 mg, 8-28 mg, 8-24 mg, 8-20 mg, 8-16 mg, 8-12 mg, 12-32 mg, 16-32 mg, 20-32 mg, 24-32 mg, 12-24 mg, 16-24 mg, 12-20 mg, or 16-20 mg; together with 250 mcg exenatide. In other embodiments, the described dosage form contains insulin in an amount of 8-32 mg, 8-28 mg, 8-24 mg, 8-20 mg, 8-16 mg, 8-12 mg, 12-32 mg, 16-32 mg, 20-32 mg, 24-32 mg, 12-24 mg, 16-24 mg, 12-20 mg, or 16-20 mg; together with 300 mcg exenatide. In other embodiments, the described dosage form contains insulin in an amount of 8-32 mg, 8-28 mg, 8-24 mg, 8-20 mg, 8-16 mg, 8-12 mg, 12-32 mg, 16-32 mg, 20-32 mg, 24-32 mg, 12-24 mg, 16-24 mg, 12-20 mg, or 16-20 mg; together with 400 mcg exenatide. In other embodiments, the described dosage form contains insulin in an amount of 8-32 mg, 8-28 mg, 8-24 mg, 8-20 mg, 8-16 mg, 8-12 mg, 12-32 mg, 16-32 mg, 20-32 mg, 24-32 mg, 12-24 mg, 16-24 mg, 12-20 mg, or 16-20 mg; together with 500 mcg exenatide. In other embodiments, the described dosage form contains insulin in an amount of 8-32 mg, 8-28 mg, 8-24 mg, 8-20 mg, 8-16 mg, 8-12 mg, 12-32 mg, 16-32 mg, 20-32 mg, 24-32 mg, 12-24 mg, 16-24 mg, 12-20 mg, or 16-20 mg; together with 600 mcg exenatide. In certain embodiments, the above dosage amounts are a daily dose.

In other embodiments, the described dosage form contains 8-16 mg insulin and 150-300 mcg. exenatide. In other embodiments, the described dosage form contains 8-12 mg insulin and 150-300 mcg. exenatide. In other embodiments, the described dosage form contains 12-16 mg insulin and 150-300 mcg. exenatide. In other embodiments, the described dosage form contains 6-16 mg insulin and 150-300 mcg. exenatide. In certain embodiments, the above dosage amounts are a daily dose.

In other embodiments, the described dosage form contains 8-16 mg insulin and 100-400 mcg. exenatide. In other embodiments, the described dosage form contains 8-12 mg insulin and 100-400 mcg. exenatide. In other embodiments, the described dosage form contains 12-16 mg insulin and 100-400 mcg. exenatide. In other embodiments, the described dosage form contains 6-16 mg insulin and 100-400 mcg. exenatide. In certain embodiments, the above dosage amounts are a daily dose.

In other embodiments, the described dosage form contains 8-16 mg insulin and 100-200 mcg. exenatide. In other embodiments, the described dosage form contains 8-12 mg insulin and 100-200 mcg. exenatide. In other embodiments, the described dosage form contains 12-16 mg insulin and 100-200 mcg. exenatide. In other embodiments, the described dosage form contains 6-16 mg insulin and 100-200 mcg. exenatide. In certain embodiments, the above dosage amounts are a daily dose.

In other embodiments, the described dosage form contains 8-16 mg insulin and 200-400 mcg. exenatide. In other embodiments, the described dosage form contains 8-12 mg insulin and 200-400 mcg. exenatide. In other embodiments, the described dosage form contains 12-16 mg insulin and 200-400 mcg. exenatide. In other embodiments, the described dosage form contains 6-16 mg insulin and 200-400 mcg. exenatide. In certain embodiments, the above dosage amounts are a daily dose.

In other embodiments, the described dosage form contains 8-16 mg insulin and 150-300 mcg. exenatide. In certain embodiments, the above dosage amounts are a daily dose.

Protease Inhibitors

Those skilled in the art will appreciate, in light of the present disclosure, that a variety or protease inhibitors may be used to protect the GLP-1 analogue and/or insulin in the described formulations. In certain embodiments, the protease inhibitor present in the described compositions is selected from a trypsin inhibitor and a chymotrypsin inhibitor. In more particular embodiments, the inhibitor is a trypsin inhibitor or, in other embodiments, is a chymotrypsin inhibitor. In still other embodiments, the pharmaceutical composition contains one or more inhibitors that collectively inhibit both trypsin and chymotrypsin. In more particular embodiments, both a trypsin inhibitor and a chymotrypsin inhibitor are present; or, in other embodiments, the protease inhibitor is a single inhibitor that inhibits both trypsin and chymotrypsin. An example of a single inhibitor that inhibits both trypsin and chymotrypsin, not intended to be limiting, is BBI (described herein).

As used herein, the term "chymotrypsin inhibitor" refers to any agent capable of inhibiting the action of chymotrypsin on a substrate. The ability of an agent to inhibit chymotrypsin can be measured using assays well known in the art. For example, in a typical assay, one unit corresponds to the amount of inhibitor that reduces the trypsin activity by one benzoyl-L-arginine ethyl ester unit (BAEE-U). One BAEE-U is the amount of enzyme that increases the absorbance at 253 nm by 0.001 per minute at pH 7.6 and 25° C. See, for example, K. Ozawa, M. Laskowski, 1966, J. Biol. Chem. 241:3955; and Y. Birk, 1976, Meth. Enzymol. 45:700.

Unless indicated otherwise, anti-chymotrypsin activity referred to herein is measured using chymotrypsin having an activity of 40 BTEE units per mg. of chymotrypsin, and is expressed in mg. of chymotrypsin inhibited per mg. of protein being tested. BTEE refers to N-Benzoyl-L-Tyrosine Ethyl Ester (see the directions for Sigma-Aldrich Product No. B6125).

As used herein, the term "trypsin inhibitor" refers to any agent capable of inhibiting the action of trypsin on a substrate. The ability of an agent to inhibit trypsin can be measured using assays well known in the art. For example, in a typical assay, one unit corresponds to the amount of inhibitor that reduces the trypsin activity by one benzoyl-L-arginine ethyl ester unit (BAEE-U). One BAEE-U is the amount of enzyme that increases the absorbance at 253 nm by 0.001 per minute at pH 7.6 and 25° C. See, for example, K. Ozawa, M. Laskowski, 1966, J. Biol. Chem. 241:3955; and Y. Birk, 1976, Meth. Enzymol. 45:700. An example of an inhibitor that inhibits trypsin, not intended to be limiting, is KTI3 (described herein).

Unless indicated otherwise, anti-trypsin activity referred to herein is measured using, trypsin having an activity of 10,000 BAEE units per mg. of trypsin, and is expressed in mg. of trypsin inhibited per mg. of protein being tested. BAEE refers to Na-Benzoyl-L-Arginine Ethyl Ester Solution (see the directions for Sigma-Aldrich Product No. B4500). For example, in a typical assay, one unit corresponds to the amount of inhibitor that reduces the trypsin activity by one benzoyl-L-arginine ethyl ester unit (BAEE-U). One BAEE-U is the amount of enzyme that increases the absorbance at 253 nm by 0.001 per minute at pH 7.6 and 25° C. See, for example, K. Ozawa, M. Laskowski, 1966, J. Biol. Chem. 241:3955; and Y. Birk, 1976, Meth. Enzymol. 45:700.

Some trypsin inhibitors known in the art are specific to trypsin, while others inhibit trypsin and other proteases such as chymotrypsin. Trypsin inhibitors can be derived from animal or vegetable sources: for example, soybean, corn, lima and other beans, squash, sunflower, bovine and other animal pancreas and lung, chicken and turkey egg white, soy-based infant formula, and mammalian blood. Trypsin inhibitors can also be of microbial origin: for example, antipain; see, for example, H. Umezawa, 1976, Meth. Enzymol. 45, 678. A trypsin inhibitor can also be an arginine or lysine mimic or other synthetic compound: for example arylguanidine, benzamidine, 3,4-dichloroisocoumarin, diisopropylfluorophosphate, gabexate mesylate, or phenylmethanesulfonyl fluoride. As used herein, an arginine or lysine mimic is a compound that is capable of binding to the $P^1$ pocket of trypsin and/or interfering with trypsin active site function.

In certain embodiments, in cases where a trypsin inhibitor is utilized in methods and compositions of the present invention, the trypsin inhibitor is selected from the group consisting of lima bean trypsin inhibitor, aprotinin, (a.k.a. pancreatic trypsin inhibitor or basic pancreatic trypsin inhibitor [BPTI]; Uniprot No. P00974 [database accessed on Jan. 2, 2013]), Kazal inhibitor (pancreatic secretory trypsin inhibitor), ovomucoid, Alpha 1-antitrypsin, Cortisol binding globulin, Centerin ([SERPINA9/GCET1 (germinal centre B-cell-expressed transcript 1)], PI-6 (Sun et al 1995), PI-8 (Sprecher et al 1995), Bomapin, a clade A serpin [for example Serpina3 (NCBI Gene ID: 12; database accessed on Dec. 27, 2012), Serpina6 (NCBI Gene ID: 866; database accessed on Dec. 27, 2012), Serpina12 (NCBI Gene ID: 145264; database accessed on Dec. 27, 2012); Serpina10 (NCBI Gene ID: 51156; database accessed on Dec. 27, 2012); Serpina7 (NCBI Gene ID: 6906; database accessed on Dec. 27, 2012); Serpina9 (NCBI Gene ID: 327657; database accessed on Dec. 27, 2012); Serpina11 (NCBI Gene ID: 256394; database accessed on Dec. 27, 2012); Serpina13 (NCBI Gene ID: 388007; database accessed on Dec. 27, 2012); Serpina2 (NCBI Gene ID: 390502; database accessed on Dec. 27, 2012); and Serpina4 (NCBI Gene ID: 5104; database accessed on Dec. 27, 2012)] Yukopin (SerpinB12; Gene ID: 89777; database accessed on Dec. 27, 2012), antipain, benzamidine, 3,4-dichloroisocoumarin, diisopropylfluorophosphate, and gabexate mesylate. In other embodiments, more than one, for example 2, 3, or 4, of the above inhibitors is selected.

A representative precursor sequence of aprotinin is:

```
                                            (SEQ ID NO: 1)
MKMSRLCLSV ALLVLLGTLA ASTPGCDTSN QAKAQRPDFC

LEPPYTGPCK ARIIRYFYNA KAGLCQTFVY GGCRAKRNNF

KSAEDCMRTC GGAIGPWENL.
```

Of these 100 residues, residues 1-21 are the signal peptide, 22-35 and 94-100 are propeptides, and the mature chain aprotinin chain is composed of residues 36-93 (58 AA).

In certain embodiments, in cases where a chymotrypsin inhibitor is utilized in methods and compositions of the present invention, the chymotrypsin inhibitor is selected from the group consisting of soybean trypsin inhibitor, Bowman-Birk inhibitor, aprotinin, N-Acetyl-eglin C from leeches (Sigma-Aldrich cat. no. E7888), chymostatin (Sigma-Aldrich cat. no. C7268), α1-antitrypsin (Sigma-Aldrich cat. no. A9024), α1-antichymotrypsin (Sigma-Aldrich cat. no. A9285), potato type I proteinase inhibitor, and potato type II proteinase inhibitor.

In other embodiments, the chymotrypsin inhibitor and/or the trypsin inhibitor is derived from soybean. Chymotrypsin and trypsin inhibitors derived from soybean (*Glycine max*) are readily available and are considered to be safe for human consumption. They include SBTI (soybean trypsin inhibitor), which in its natural form is composed of KTI3 (Kunitz Trypsin Inhibitor 3), which inhibits trypsin, and BBI (Bowman-Birk inhibitor; Uniprot number P01055 [database accessed on Jan. 3, 2013]), which inhibits chymotrypsin and trypsin. The term "SBTI", as used herein, refers, unless indicated otherwise, to a combination of KTI3 and BBI, which may be a naturally occurring combination or an artificial combination of KTI3 and BBI. In accordance with accepted usage in the art, SBTI is sometimes referred to herein as a single protease inhibitor, despite the fact that it has two separate protease components.

Chymotrypsin and trypsin inhibitor are available for example from Sigma-Aldrich, St. Louis, Mo., USA.

In certain embodiments, SBTI is present in an amount between 25-125 mg per dosage unit when present with another inhibitor of chymotrypsin and/or trypsin and 75-200 mg per dosage unit when present as the only inhibitor of chymotrypsin and/or trypsin. In various embodiments, SBTI is present in an amount of 30-180 mg, 35-170 mg, 40-160 mg, 45-150 mg, 50-140 mg, 50-130 mg, 50-120 mg, 50-100 mg, 55-95 mg, 60-90 mg, 65-85 mg, 70-80 mg, 50-150 mg, 60-140 mg, 70-130 mg, 80-120 mg, 90-100 mg, 100-150 mg, 110-140 mg, 120-130 mg, 100-200 mg, 110-190 mg, 120-180 mg, 130-170 mg, or 140-160 mg per dosage unit. All the aforementioned ranges are inclusive. In still other embodiments, the SBTI is present in an amount of 25 mg, 30 mg, 40 mg, 50 mg, 60 mg, 75 mg, 90 mg, 100 mg, 110 mg, 125 mg, 150 mg, 175 mg, or 200 mg per dosage unit.

Methods for preparing BBI are described for example in U.S. Pat. No. 7,404,973 and in PCT International Application Publ. No. WO 2013/10289 to Avraham Hershko, filed on Jan. 31, 2013, the contents of which are incorporated herein by reference.

A representative precursor sequence of BBI is:

```
                                      (SEQ ID NO: 2)
MVVLKVCLVL LFLVGGTTSA NLRLSKLGLL MKSDHQHSND

DESSKPCCDQ CACTKSNPPQ CRCSDMRLNS CHSACKSCIC

ALSYPAQCFC VDITDFCYEP CKPSEDDKEN.
```

Of these 110 residues, residues 1-19 are the signal peptide, 20-39 are a propeptide, and the mature chain BBI chain is composed of residues 40-110 (71 AA).

In certain embodiments, BBI is present in an amount between 25-125 mg per dosage unit when present with another inhibitor of chymotrypsin and/or trypsin and 75-200 mg per dosage unit when present as the only inhibitor of chymotrypsin and/or trypsin. In various embodiments, BBI is present in an amount of 30-180 mg, 35-170 mg, 40-160 mg, 45-150 mg, 50-140 mg, 50-130 mg, 50-120 mg, 50-100 mg, 55-95 mg, 60-90 mg, 65-85 mg, 70-80 mg, 50-150 mg, 60-140 mg, 70-130 mg, 80-120 mg, 90-100 mg, 100-150 mg, 110-140 mg, 120-130 mg, 100-200 mg, 110-190 mg, 120-180 mg, 130-170 mg, or 140-160 mg per dosage unit. All the aforementioned ranges are inclusive. In still other embodiments, the BBI is present in an amount of 25 mg, 30 mg, 40 mg, 50 mg, 60 mg, 75 mg, 90 mg, 100 mg, 110 mg, 125 mg, 150 mg, 175 mg, or 200 mg per dosage unit.

In one aspect, a BBI utilized in the described methods and compositions is at least 85% pure as measured, in various embodiments, by sodium dodecyl sulfate polyacrylamide gel electrophoresis (SDS-PAGE), Brilliant Blue staining, or imager quantitation. In certain embodiments, the soybean product is soy flour.

In yet another aspect, the protein content of the BBI is greater than 95% by BCA (bicinchoninic acid) assay.

In yet another aspect the BBI utilized in the described methods and compositions contains less than 0.1% high-MW contaminants, for example as assessed by SDS-PAGE and imager quantitation.

In other embodiments, the isolated BBI has an anti-chymotrypsin activity of at least 0.8, 0.9, 1.0, 1.1, 1.2, 1.3, or 1.4 mg. chymotrypsin inhibited per mg. inhibitor. In other embodiments, the anti-chymotrypsin activity is in the range of 0.8-1.8, 0.9-1.8, 1.0-1.8, 1.1-1.8, 1.2-1.8, 1.3-1.8, or 1.4-1.8 mg. chymotrypsin inhibited per mg. inhibitor. In more specific embodiments, the activity is 0.8-1.8 mg. chymotrypsin inhibited per mg. inhibitor. In other embodiments, the activity is in the range of 0.8-1.5 mg. chymotrypsin inhibited per mg. inhibitor. In the context of a pharmaceutical composition, this value refers to characteristics of the BBI prior to its being mixed with one or more other components of the pharmaceutical composition.

Those skilled in the art will appreciate that each of the above purity requirements, regarding its protein content, level of contaminants, or potency, is typically assessed prior to the BBI being mixed with any of the other components of the pharmaceutical composition. Various purified types of BBI are disclosed in PCT International Application Publ. No. WO 2013/10289 to Avraham Hershko, filed on Jan. 31, 2013, the contents of which are incorporated herein by reference.

In other embodiments, the isolated BBI in the described methods and compositions is a recombinant BBI, for example BBI produced by a microorganism such as a bacterium that has been engineered to express it and subsequently isolated. In still other embodiments, the BBI is a synthetic BBI. An example of a synthetic BBI is BBI that has been produced in a cell-free apparatus such as a peptide synthesizer. Peptide synthesizers, for example automated peptide synthesizers, are well known in the art and are available commercially. Pharmaceutical compositions comprising recombinant BBI are also provided herein. Pharmaceutical compositions comprising synthetic BBI are also provided herein.

In certain embodiments, the described BBI is the only protease inhibitor in the described methods and compositions. While lower-potency SBTI requires an additional protease inhibitor, e.g. aprotinin, to efficiently protect certain therapeutic proteins in the human digestive tract, the described isolated BBI is, in some embodiments, capable of reducing the need for additional protease inhibitors in this regard.

Methods for preparing KTI3 are described for example in PCT International Application Publ. No. WO 2013/102899 to Avraham Hershko, filed on Jan. 31, 2013, the contents of which are incorporated herein by reference.

KTI3 has Uniprot number P01070 (database accessed on Jan. 3, 2013). A representative precursor sequence of KTI3 is:

```
                                          (SEQ ID NO: 3)
MKSTIFFLFL  FCAFTTSYLP  SAIADFVLDN  EGNPLENGGT

YYILSDITAF  GGIRAAPTGN  ERCPLTVVQS  RNELDKGIGT

IISSPYRIRF  IAEGHPLSLK  FDSFAVIMLC  VGIPTEWSVV

EDLPEGPAVK  IGENKDAMDG  WFRLERVSDD  EFNNYKLVFC

PQQAEDDKCG  DIGISIDHDD  GTRRLVVSKN  KPLVVQFQKL

DKESLAKKNH  GLSRSE.
```

Of the above sequence, residues 1-24 are the signal peptide, 206-216 are a propeptide, and the mature KTI3 chain is composed of residues 25-205 (181 AA).

In certain embodiments, KTI3 is present in an amount between 25-125 mg per dosage unit and is present with a chymotrypsin inhibitor. In various embodiments, KTI3 is present in an amount of 30-120 mg, 35-115 mg, 40-110 mg, 45-105 mg, 50-100 mg, 55-95 mg, 60-90 mg, 65-85 mg, 70-80 mg, 25-100 mg, 30-90 mg, 35-80 mg, 35-70 mg, 40-60 mg, 45-55 mg, 80-120 mg, 85-115 mg, 90-100 mg, or 95-105 mg per dosage unit. All the aforementioned ranges are inclusive. In still other embodiments, the KTI3 is present in an amount of 25 mg, 30 mg, 40 mg, 50 mg, 60 mg, 75 mg, 90 mg, 100 mg, 110 mg, or 120 mg per dosage unit.

In an additional aspect, a KTI3 utilized in the described methods and compositions is at least 85% pure as measured, in various embodiments, by SDS-PAGE, Brilliant Blue staining, or imager quantitation.

In yet another aspect, the protein content of the KTI3 is greater than 95% as measured by BCA assay.

In yet another aspect, the KTI3 contains less than 0.1% high-MW contaminants, for example as assessed by SDS-PAGE and imager quantitation.

In other embodiments, the isolated KTI3 has an anti-trypsin activity of at least 0.8, 0.9, 1.0, 1.1, 1.2, or 1.3 mg. trypsin inhibited per mg. inhibitor. In other embodiments, the activity of the KTI3 is in the range of 0.8-1.8, 0.9-1.8, 1.0-1.8, 1.1-1.8, 1.2-1.8, or 1.3-1.8 mg. trypsin inhibited per mg. inhibitor. In more particular embodiments, the activity of the KTI3 is 0.8-1.7 mg. trypsin inhibited per mg. inhibitor. In other embodiments, the activity is range of 0.8-1.4 mg. trypsin inhibited per mg. inhibitor.

In other preferred embodiments, the isolated KTI is a recombinant KTI, for example KTI produced by a microorganism such as a bacterium that has been engineered to express it. In still other preferred embodiments, the KTI is a synthetic KTI. An example of a synthetic KTI is KTI that has been produced in a cell-free apparatus such as a peptide synthesizer.

Those skilled in the art will appreciate that each of the above purity requirements, regarding its protein content, level of contaminants, or potency, is typically assessed prior to the KTI3 being mixed with any of the other components of the pharmaceutical composition. Various purified types of KTI are disclosed in PCT International Application Publ. No. WO 2013/10289 to Avraham Hershko, filed on Jan. 31, 2013, the contents of which are incorporated herein by reference.

Other embodiments concern the ratio of the anti-chymotrypsin activity present in the described pharmaceutical composition to the anti-trypsin activity of the composition. In some embodiments, this parameter is between 1.5:1 and 1:1. In more specific embodiments, the ratio may be between 1.4:1-1.1:1. In more specific embodiments, the ratio may be between 1.35:1-1.2:1.

In still other embodiments, the described purified SBTI, BBI, and/or KTI is present together with at least one of the described emulsifiers, in some embodiments in combination with at least one of the described non-ionic detergents. Each described embodiment of the purified SBTI, BBI, and/or KTI may be freely combined with the described embodiments of emulsifiers and/or non-ionic detergents.

Combinations of Protease Inhibitors

In certain embodiments, the pharmaceutical composition utilized in the described methods and compositions comprises a combination of an isolated BBI and another protease inhibitor, for example a trypsin inhibitor. In other embodiments, the pharmaceutical composition comprises a combination of an isolated KTI3 and another protease inhibitor. Those skilled in the art will appreciate in light of the present disclosure that a variety of protease inhibitors, including those mentioned hereinabove, may be utilized. In the case of protease inhibitors that are proteins, the size will typically be up to 100 kDa.

In other embodiments, the pharmaceutical composition utilized in the described methods and compositions comprises both isolated BBI and isolated KTI, in more specific embodiments both isolated BBI and isolated KTI3. The terms "isolated KTI3 and "isolated BBI" as used herein refers to a preparation enriched in the named component relative to other component of SBTI (i.e. BBI or KTI3, respectively). In various embodiments, the preparation of KTI utilized in the described methods and compositions is at least 85% pure as assessed by SDS-PAGE, Brilliant Blue staining, or imager quantitation (e.g. according to the protocol described herein). In other embodiments, the protein content of the KTI preparation is greater than 95% by BCA assay. In the context of a pharmaceutical composition, these values refer to characteristics of the KTI prior to its being mixed with one or more other components of the pharmaceutical composition. In other embodiments, the KTI preparation contains 5% or less BBI as assessed by SDS-PAGE. In other embodiments, the KTI preparation contains less than 0.1% high-MW contaminants (in other words, substances having a MW of greater than 30,000).

In yet other embodiments, the weight/weight (w/w) ratio of BBI to KTI3 in the pharmaceutical composition is between 1.5:1 and 2.5:1, in other embodiments between 1.6:1 and 2.4:1, in other embodiments between 1.7:1 and 2.3:1, in other embodiments between 1.8:1 and 2.2:1, in other embodiments between 1.9:1 and 2.1:1, in other embodiments between 1.95:1 and 2.05:1, in other embodiments 2:1.

In still more specific embodiments, the described methods and compositions comprise the described BBI and KTI, in more specific embodiments BBI and KTI3, as the only protease inhibitors. In other embodiments, the described methods and compositions comprise KTI and aprotinin, in more specific embodiments KTI3 and aprotinin, as the only protease inhibitors. In other embodiments, isolated BBI, isolated KTI, and aprotinin are all present in the pharmaceutical composition.

In yet other embodiments, BBI and KTI3 are present in amounts of 50-100 and 25-50 mg, respectively, per dosage form, and are the only protease inhibitors in the composition. In other embodiments, the amounts are 55-90 and 25-45 mg, respectively; 60-90 and 25-45 mg, respectively; 60-85 and 25-45 mg, respectively; 60-80 and 25-45 mg, respectively; 65-75 and 30-40 mg, respectively; 68-72 and 33-37 mg, respectively; or 70 and 35 mg, respectively. In still other embodiments, the aforementioned amounts of BBI and KTI3 are present together with another trypsin inhibitor, for example aprotinin.

In still other embodiments, the described combinations of protease inhibitors are present together with the described emulsifiers, in some embodiments in combination with the described non-ionic detergents. Each described combination of protease inhibitors may be freely combined with the described embodiments of emulsifiers and/or non-ionic detergents.

Chelators of Divalent Cations

The chelator of divalent cations utilized in the described methods and compositions is, in one embodiment, any physiologically acceptable compound having a high affinity for at least one of calcium, magnesium, and manganese ions. In another embodiment, the chelator is selected from the group consisting of citrate or a salt thereof; ethylenediamine tetracetic acid (EDTA) or a salt thereof (for example disodium EDTA and calcium disodium EDTA); EGTA (ethylene glycol tetraacetic acid) or a salt thereof; diethylene triamine pentaacetic acid (DTPA) or a salt thereof; and BAPTA (1,2-bis(o-aminophenoxy)ethane-N,N,N',N'-tetraacetic acid) or a salt thereof. In other embodiments, one of the above-listed chelators is utilized. In more specific embodiments, the chelator is EDTA.

Oils

Certain embodiments of pharmaceutical compositions and methods described herein comprise a liquid phase, wherein one or more oils is utilized as the basis of the liquid phase. In certain embodiments, the oil may be any physiologically acceptable oil that is liquid at ambient temperature.

Reference herein to components which are "in an oil" or "in a liquid" means that each of the named components are dissolved, suspended, and/or emulsified in an oil or oil phase. Reference to "oil-based" compositions means that all the solid components of the compositions (i.e. the components that are usually provided as a solid in a tableting process) are dissolved, suspended, and/or emulsified in an oil or oil phase. In some embodiments, an oil phase is the only liquid component of the pharmaceutical composition. In more specific embodiments, the oil phase is the only component of the pharmaceutical composition, other than the capsule and optional other coatings.

In other embodiments, the oil-based liquid phase of the pharmaceutical composition is water-free, or in other embodiments is alcohol-free, or in other embodiments is both alcohol-free and water-free. In other embodiments, the oil or mixture of oils are the only liquid components of the oil phase other than one or more optional emulsifiers or surfactants. In still other embodiments, the oil or mixture of oils are the only liquid components of the oil phase.

In yet other embodiments, the oil phase consists of the oil or mixture of oils and the solid components dissolved, suspended, and/or emulsified therein. In yet other embodiments, the oil phase consists of the oil or mixture of oils and one or more therapeutic proteins, one or more protease inhibitors, and a chelator of divalent cations, all of which are dissolved, suspended, and/or emulsified therein. In yet other embodiments, the oil phase consists of the oil or mixture of oils; one or more therapeutic proteins, one or more protease inhibitors, and a chelator of divalent cations, all of which are dissolved, suspended, and/or emulsified therein; and one or more optional emulsifiers or surfactants. Trace liquid components, such as water absorbed from the atmosphere, is not considered to be present for purposes of classifying a composition as "water-free", having an oil or mixture of oils as the "only liquid components", or the like.

In more specific embodiments, the oil comprises an omega-3 fatty acid. In other embodiments, the omega-3 fatty acid is an omega-3 polyunsaturated fatty acid. In another embodiment, the omega-3 fatty acid is DHA, an omega-3, polyunsaturated, 22-carbon fatty acid also referred to as 4, 7, 10, 13, 16, 19-docosahexaenoic acid. In another embodiment, the omega-3 fatty acid is linolenic acid (9, 12, 15-octadecatrienoic acid). In another embodiment, the omega-3 fatty acid is stearidonic acid (6, 9, 12, 15-octadecatetraenoic acid). In another embodiment, the omega-3 fatty acid is eicosatrienoic acid (ETA; 11, 14, 17-eicosatrienoic acid). In another embodiment, the omega-3 fatty acid is eicsoatetraenoic acid (8, 11, 14, 17-eicosatetraenoic acid). In one embodiment, the omega-3 fatty acid is eicosapentaenoic acid (EPA; 5, 8, 11, 14, 17-eicosapentaenoic acid). In another embodiment, the omega-3 fatty acid is eicosahexaenoic acid (also referred to as 5, 7, 9, 11, 14, 17-eicosahexaenoic acid). In another embodiment, the omega-3 fatty acid is docosapentaenoic acid (DPA; 7, 10, 13, 16, 19-docosapentaenoic acid). In another embodiment, the omega-3 fatty acid is tetracosahexaenoic acid (6, 9, 12, 15, 18, 21-tetracosahexaenoic acid).

In other embodiments, the oil is a naturally-occurring oil comprising an omega-3 fatty acid. In other embodiments, the oil is a naturally-occurring oil that is generally recognized as safe (GRAS). In other embodiments, the oil is a naturally-occurring GRAS vegetable oil. In certain embodiments, the oil may be selected from cardamom oil, carrot seed oil, Roman chamomile oil, coriander oil, black cumin oil, goldenrod oil, mandarin oil, lemon balm oil, sandalwood oil, spearmint oil, olive oil, flaxseed oil, sesame oil, avocado oil, walnut oil, canola oil, cottonseed oil, corn oil, safflower oil, sunflower oil, soybean oil, grapeseed oil, almond oil, and fish oil, non-limiting examples of which are salmon oil and tuna oil. In more specific embodiments, the oil may be selected from olive oil, flaxseed oil, sesame oil, avocado oil, walnut oil, canola oil, and fish oil. In still more specific embodiments, the oil is selected from fish oil, canola oil, and flaxseed oil. Alternatively, the oil is selected from the group consisting of fish oil, canola oil, flaxseed oil, algal oil and hemp seed oil. In more specific embodiments, the oil is a fish oil. Several types of fish oil have been tested in the compositions described herein and have all been found to work equally well.

Neurodegenerative Disorders

It will be appreciated by those skilled in the art GLP-1 can have a therapeutic effect on neurodegenerative disorders independently of its effects on NAFLD. Those skilled in the art will appreciate that neurodegenerative disorders can be diagnosed by a number of known methods, including MRI (magnetic resonance imaging) of the central nervous system.

Provided herein, in another embodiment, is a pharmaceutical composition for treating, or in another aspect reducing the incidence of, Alzheimer's disease, said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

Still another aspect provides a method of treating, or in another aspect reducing the incidence of, Alzheimer's disease, the method comprising the step of administering to a subject a pharmaceutical composition described hereinabove, thereby treating or reducing the incidence of Alzheimer's disease.

Provided herein, in another embodiment, is a pharmaceutical composition for treating, or in another aspect reducing the incidence of, Parkinson's disease, said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

Still another aspect provides a method of treating, or in another aspect reducing the incidence of, Parkinson's disease, the method comprising the step of administering to a subject a pharmaceutical composition described hereinabove, thereby treating or reducing the incidence of Parkinson's disease.

Provided herein, in another embodiment, is a pharmaceutical composition for treating, or in another aspect reducing the incidence of, Huntington's disease, said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

Still another aspect provides a method of treating, or in another aspect reducing the incidence of, Huntington's disease, the method comprising the step of administering to a subject a pharmaceutical composition described hereinabove, thereby treating or reducing the incidence of Huntington's disease.

Provided herein, in another embodiment, is a pharmaceutical composition for treating, or in another aspect reducing the incidence of, ALS, said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

Still another aspect provides a method of treating, or in another aspect reducing the incidence of, ALS, the method comprising the step of administering to a subject a pharmaceutical composition described hereinabove, thereby treating or reducing the incidence of ALS.

Provided herein, in another embodiment, is a pharmaceutical composition for treating, or in another aspect reducing the incidence of, traumatic brain injury (TBI), said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

Still another aspect provides a method of treating, or in another aspect reducing the incidence of, TBI, the method comprising the step of administering to a subject a pharmaceutical composition described hereinabove, thereby treating or reducing the incidence of TBI.

Provided herein, in another embodiment, is a pharmaceutical composition for treating, or in another aspect reducing the incidence of, mood disorders, said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

Still another aspect provides a method of treating, or in another aspect reducing the incidence of, mood disorders, the method comprising the step of administering to a subject a pharmaceutical composition described hereinabove, thereby treating or reducing the incidence of mood disorders.

Provided herein, in another embodiment, is a pharmaceutical composition for reducing tissue damage from cerebral stroke, said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

Still another aspect provides a method of reducing tissue damage from cerebral stroke, the method comprising the step of administering to a subject a pharmaceutical composition described hereinabove, thereby reducing tissue damage from cerebral stroke.

Provided herein, in another embodiment, is a pharmaceutical composition for treating, or in another aspect reducing the incidence of, retinal degeneration, said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

Still another aspect provides a method of treating, or in another aspect reducing the incidence of, retinal degeneration, the method comprising the step of administering to a subject a pharmaceutical composition described hereinabove, thereby treating or reducing the incidence of retinal degeneration.

Provided herein, in another embodiment, is a pharmaceutical composition for treating, or in another aspect reducing the incidence of, peripheral neuropathy (PN), said pharmaceutical composition comprising insulin, a GLP-1 analogue, at least one protease inhibitor, and a chelator of divalent cations. In another embodiment, the pharmaceutical composition comprises a GLP-1 analogue, at least one protease inhibitor, and a chelator of divalent cations. In certain embodiments, the pharmaceutical composition comprises one of the oil-based liquid formulations described herein, wherein the pharmaceutical composition may further comprise, in some embodiments, a capsule and/or coating that resists degradation in the stomach. In other embodiments, the pharmaceutical composition comprises one of the solid formulations described herein. In certain embodiments, the pharmaceutical composition is administered to the subject for an extended time.

Still another aspect provides a method of treating, or in another aspect reducing the incidence of, PN, the method comprising the step of administering to a subject a pharmaceutical composition described hereinabove, thereby treating or reducing the incidence of PN.

Representative Specific Formulations

In certain embodiments, a formulation utilized in the described methods and compositions is a liquid formulation that comprises insulin, a GLP-1 analogue, and at least one trypsin inhibitor, all of which are in an oil, for example dissolved, suspended, and/or emulsified in the oil. In more specific embodiments, the GLP-1 analogue may be exenatide. In other embodiments, the described liquid formulation comprises insulin, a GLP-1 analogue, and at least one chymotrypsin inhibitor. In still other embodiments, the described liquid formulation comprises insulin, a GLP-1 analogue, at least one trypsin inhibitor, and at least one chymotrypsin inhibitor. In still other embodiments, the described liquid formulation comprises insulin, a GLP-1 analogue, one trypsin inhibitor, and one chymotrypsin inhibitor. In more specific embodiments, the protease inhibitors are SBTI and aprotinin. Alternatively, purified KTI3 and aprotinin are utilized. In still other embodiments, purified BBI is the only protease inhibitor present. In other embodiments, a chelator of divalent cations is also present in the liquid formulation, which is, in more specific embodiments, EDTA. Alternatively or in addition, the liquid formulation is in a gelatin capsule. In more specific embodiments, the gelatin capsule is coated with an enteric coating.

Reference herein to a trypsin inhibitor in combination with a chymotrypsin inhibitor encompasses cases where a trypsin inhibitor such as KTI3 is present together with an inhibitor of both chymotrypsin and trypsin.

In certain embodiments, a formulation utilized in the described methods and compositions is a liquid formulation that comprises insulin and at least one trypsin inhibitor, both/all of which are in an oil, for example dissolved, suspended, and/or emulsified in the oil. In other embodiments, the described liquid formulation comprises insulin and at least one chymotrypsin inhibitor. In still other embodiments, the described liquid formulation comprises insulin, at least one trypsin inhibitor, and at least one chymotrypsin inhibitor. In still other embodiments, the described liquid formulation comprises insulin, one trypsin inhibitor, and one chymotrypsin inhibitor. In more specific embodiments, the protease inhibitors are SBTI and aprotinin. Alternatively, purified KTI3 and aprotinin are utilized. In still other embodiments, purified BBI is the only protease inhibitor present. In other embodiments, a chelator of divalent cations is also present in the liquid formulation, which is, in more specific embodiments, EDTA. Alternatively or in addition, the liquid formulation is in a gelatin capsule. In more specific embodiments, the gelatin capsule is coated with an enteric coating.

In certain embodiments, a formulation utilized in the described methods and compositions is a liquid formulation that comprises a GLP-1 analogue and at least one trypsin inhibitor, both/all of which are in an oil, for example dissolved, suspended, and/or emulsified in the oil. In more specific embodiments, the GLP-1 analogue may be exenatide. In other embodiments, the described liquid formulation comprises a GLP-1 analogue and at least one chymotrypsin inhibitor. In still other embodiments, the described liquid formulation comprises a GLP-1 analogue, at least one trypsin inhibitor, and at least one chymotrypsin inhibitor. In still other embodiments, the described liquid formulation comprises a GLP-1 analogue, one trypsin inhibitor, and one chymotrypsin inhibitor. In more specific embodiments, the protease inhibitors are SBTI and aprotinin. Alternatively, purified KTI3 and aprotinin are utilized. In still other embodiments, purified BBI is the only protease inhibitor present. In other embodiments, a chelator of divalent cations is also present in the liquid formulation, which is, in more specific embodiments, EDTA. Alternatively or in addition, the liquid formulation is in a gelatin capsule. In more specific embodiments, the gelatin capsule is coated with an enteric coating.

In other embodiments, a liquid formulation utilized in the described method or composition comprises insulin, exenatide, a surfactant, EDTA, SBTI, aprotinin, and oil. In some embodiments, the surfactant referred to in this paragraph may be Gelucire 44/14. In other embodiments, the liquid formulation consists essentially of insulin, exenatide, a surfactant, EDTA, SBTI, aprotinin, and oil. "Consists essentially of" in this and the below paragraphs indicates that the liquid formulation does not contain any other components that appreciably affect its physiological characteristics. In other embodiments, the liquid formulation consists of insulin, exenatide, a surfactant, EDTA, SBTI, aprotinin, and oil. In other, even more specific embodiments, the amounts of insulin, exenatide, EDTA, SBTI, aprotinin, and oil per dosage form are 8-16 mg, 150-300 mcg, 100-200 mg, 50-100 mg, 20-30 mg, and 0.4-0.7 ml, respectively, and the amount of surfactant, e.g. Gelucire 44/14, is 8-16%. In still more specific embodiments, the amounts of insulin, exenatide, EDTA, SBTI, aprotinin, and oil per dosage form are 8-16 mg, 150-300 mcg, 150 mg, 65-85 mg, 22-26 mg, and 0.5-0.7 ml, respectively, and the amount of surfactant, e.g. Gelucire 44/1444/14 is 8-16%. An even more specific embodiment comprises 75 mg SBTI and 24 mg aprotinin. In other embodiments, the above composition further comprises polysorbate 80. In some embodiments, the polysorbate 80 constitutes 3-10% weight/weight inclusive of the oil-based liquid formulation. In certain embodiments, all the aforementioned ingredients (other than the oil) are all provided in the oil, for example dissolved or suspended in the oil, which is, in some embodiments, one of the oils mentioned herein. Alternatively or in addition, the above composition is coated by a coating that resists degradation in the stomach. Alternatively or in addition, purified KTI3 is present in place of SBTI in one of the amounts mentioned above. In various embodiments, purified BBI is the only protease inhibitor present and is present in an amount of 50-200 mg, in other embodiments 75-200 mg, in other embodiments 75-180 mg, in other embodiments 75-150 mg, in other embodiments 75-125 mg, in other embodiments 90-110 mg, in other embodiments 100-150 mg, in other embodiments 110-140 mg, in other embodiments 120-130 mg, in other embodiments 120-160 mg, in other embodiments 130-150 mg, in other embodiments 75 mg, in other embodiments 100 mg, in other embodiments 125 mg, in other embodiments 150 mg, in other embodiments 175 mg, in other embodiments 200 mg.

In more specific embodiments, a liquid formulation utilized in the described method or composition comprises insulin; exenatide; a self-emulsifying component, for example a component provided as a mixture of (a) a monoacylglycerol, a diacylglycerol, a triacylglycerol, or a mixture thereof; and (b) a PEG ester of a fatty acid; EDTA; SBTI; aprotinin; and oil. In other embodiments, the liquid formulation consists essentially of insulin, exenatide, a self-emulsifying component, EDTA, SBTI, aprotinin, and oil. In other embodiments, the liquid formulation consists of insulin, exenatide, a self-emulsifying component, EDTA, SBTI, aprotinin, and oil. In other, even more specific embodiments, the amounts of insulin, exenatide, EDTA, SBTI, aprotinin, and oil per dosage form are 8-16 mg, 150-300 mcg, 100-200 mg, 50-100 mg, 20-30 mg, and 0.4-0.7 ml, respectively, and the amount of self-emulsifying component is 8-16%. In still more specific embodiments, the amounts of insulin, exenatide, EDTA, SBTI, aprotinin, and oil per dosage form are 8-16 mg, 150-300 mcg, 150 mg, 65-85 mg, 22-26 mg, and 0.5-0.7 ml, respectively, and the amount of self-emulsifying component is 8-16%. An even more specific embodiment comprises 75 mg SBTI and 24 mg aprotinin. In other embodiments, the above composition further comprises polysorbate 80. In certain embodiments, the polysorbate 80 constitutes 3-10% (inclusive) weight/weight of the oil-based liquid formulation. In certain embodiments, all the aforementioned ingredients other than the oil are provided in the oil, for example dissolved or suspended in the oil, which is, in some embodiments, one of the oils mentioned herein. Alternatively or in addition, the above composition is coated by a coating that resists degradation in the stomach. Alternatively or in addition, purified KTI3 is present in place of SBTI in one of the amounts mentioned above. In other embodiments, purified BBI is present in one of the amounts mentioned above for SBTI and is the only protease inhibitor present.

In other embodiments, a liquid formulation utilized in the described method or composition comprises exenatide, a surfactant, EDTA, SBTI, aprotinin, and oil. In some embodiments, the surfactant referred to in this paragraph may be Gelucire 44/14. In other embodiments, the liquid formulation consists essentially of exenatide, a surfactant, EDTA, SBTI, aprotinin, and oil. In other embodiments, the liquid formulation consists of exenatide, a surfactant, EDTA, SBTI, aprotinin, and oil. In other, even more specific embodiments, the amounts of exenatide, EDTA, SBTI, aprotinin, and oil per dosage form are 150-300 mcg, 100-200 mg, 50-100 mg, 20-30 mg, and 0.4-0.7 ml, respectively, and the amount of a surfactant, e.g. Gelucire 44/14 is 8-16%. In still more specific embodiments, the amounts of exenatide, EDTA, SBTI, aprotinin, and oil per dosage form are 150-300 mcg, 150 mg, 65-85 mg, 22-26 mg, and 0.5-0.7 ml, respectively, and the amount of surfactant, e.g. Gelucire 44/1444/14 is 8-16%. An even more specific embodiment comprises 75 mg SBTI and 24 mg aprotinin. In other embodiments, the above composition further comprises polysorbate 80. In some embodiments, the polysorbate 80 constitutes 3-10% weight/weight inclusive of the oil-based liquid formulation. In certain embodiments, all the aforementioned ingredients other than the oil are provided in the oil, for example dissolved or suspended in the oil, which is, in some embodiments, one of the oils mentioned herein. Alternatively or in addition, the above composition is coated by a coating that resists degradation in the stomach. Alternatively or in addition, purified KTI3 is present in place of SBTI in one of the amounts mentioned above. In various embodiments, purified BBI is the only protease inhibitor present and is present in an amount of 50-200 mg, in other embodiments 75-200 mg, in other embodiments 75-180 mg, in other embodiments 75-150 mg, in other embodiments 75-125 mg, in other embodiments 90-110 mg, in other embodiments 100-150 mg, in other embodiments 110-140 mg, in other embodiments 120-130 mg, in other embodiments 120-160 mg, in other embodiments 130-150 mg, in other embodiments 75 mg, in other embodiments 100 mg, in other embodiments 125 mg, in other embodiments 150 mg, in other embodiments 175 mg, in other embodiments 200 mg.

In still more specific embodiments, a liquid formulation utilized in the described method or composition comprises exenatide, a self-emulsifying component, EDTA, SBTI, aprotinin, and oil. In other embodiments, the liquid formulation consists essentially of exenatide, a self-emulsifying component, EDTA, SBTI, aprotinin, and oil. In other embodiments, the liquid formulation consists of exenatide, a self-emulsifying component, EDTA, SBTI, aprotinin, and oil. In other, even more specific embodiments, the amounts of exenatide, EDTA, SBTI, aprotinin, and oil per dosage form are 150-300 mcg, 100-200 mg, 50-100 mg, 20-30 mg, and 0.4-0.7 ml, respectively, and the amount of self-emulsifying component is 8-16%. In still more specific embodiments, the amounts of exenatide, EDTA, SBTI, aprotinin, and oil per dosage form are 150-300 mcg, 150 mg, 65-85 mg, 22-26 mg, and 0.5-0.7 ml, respectively, and the amount of self-emulsifying component is 8-16%. An even more specific embodiment comprises 75 mg SBTI and 24 mg aprotinin. In other embodiments, the above composition further comprises polysorbate 80. In certain embodiments, the polysorbate 80 constitutes 3-10% weight/weight inclusive of the oil-based liquid formulation. In certain embodiments, all the aforementioned ingredients other than the oil are provided in the oil, for example dissolved or suspended in the oil, which is, in some embodiments, one of the oils mentioned herein. Alternatively or in addition, the above composition is coated by a coating that resists degradation in the stomach. Alternatively or in addition, purified KTI3 is present in place of SBTI in one of the amounts mentioned above. In various embodiments, purified BBI is the only protease inhibitor present and is present in an amount of 50-200 mg, in other embodiments 75-200 mg, in other embodiments 75-180 mg, in other embodiments 75-150 mg, in other embodiments 75-125 mg, in other embodiments 90-110 mg, in other embodiments 100-150 mg, in other embodiments 110-140 mg, in other embodiments 120-130 mg, in other embodiments 120-160 mg, in other embodiments 130-150 mg, in other embodiments 75 mg, in other embodiments 100 mg, in other embodiments 125 mg, in other embodiments 150 mg, in other embodiments 175 mg, in other embodiments 200 mg.

In other embodiments, a liquid formulation utilized in the described method or composition comprises insulin, Gelucire 44/14, EDTA, SBTI, aprotinin, and oil. In other embodiments, the liquid formulation consists essentially of insulin, Gelucire 44/14, EDTA, SBTI, aprotinin, and oil. In other embodiments, the liquid formulation consists of insulin, Gelucire 44/14, EDTA, SBTI, aprotinin, and oil. In other, even more specific embodiments, the amounts of insulin, EDTA, SBTI, aprotinin, and oil per dosage form are 8-16 mg, 100-200 mg, 50-100 mg, 20-30 mg, and 0.4-0.7 ml, respectively, and the amount of Gelucire 44/14 is 8-16%. In still more specific embodiments, the amounts of insulin, EDTA, SBTI, aprotinin, and oil per dosage form are 8-16 mg, 150 mg, 65-85 mg, 22-26 mg, and 0.5-0.7 ml, respectively, and the amount of Gelucire 44/14 is 8-16%. An even more specific embodiment comprises 75 mg SBTI and 24 mg aprotinin. In other embodiments, the above composition further comprises polysorbate 80. In some embodiments, the polysorbate 80 constitutes 3-10% weight/weight inclusive of the oil-based liquid formulation. In certain embodiments, all the aforementioned ingredients other than the oil are provided in the oil, for example dissolved or suspended in the oil, which is, in some embodiments, one of the oils mentioned herein. Alternatively or in addition, the above composition is coated by a coating that resists degradation in the stomach. Alternatively or in addition, purified KTI3 is present in place of SBTI in one of the amounts mentioned above. In various embodiments, purified BBI is the only protease inhibitor present and is present in an amount of 50-200 mg, in other embodiments 75-200 mg, in other embodiments 75-180 mg, in other embodiments 75-150 mg, in other embodiments 75-125 mg, in other embodiments 90-110 mg, in other embodiments 100-150 mg, in other embodiments 110-140 mg, in other embodiments 120-130 mg, in other embodiments 120-160 mg, in other embodiments 130-150 mg, in other embodiments 75 mg, in other embodiments 100 mg, in other embodiments 125 mg, in other embodiments 150 mg, in other embodiments 175 mg, in other embodiments 200 mg.

In still more specific embodiments, a liquid formulation utilized in the described method or composition comprises insulin, a self-emulsifying component, EDTA, SBTI, aprotinin, and oil. In other embodiments, the liquid formulation consists essentially of insulin, a self-emulsifying component, EDTA, SBTI, aprotinin, and oil. In other embodiments, the liquid formulation consists of insulin, a self-emulsifying component, EDTA, SBTI, aprotinin, and oil. In other, even more specific embodiments, the amounts of insulin, EDTA, SBTI, aprotinin, and oil per dosage form are 8-16 mg, 100-200 mg, 50-100 mg, 20-30 mg, and 0.4-0.7 ml, respectively, and the amount of self-emulsifying component is 8-16%. In still more specific embodiments, the amounts of insulin, EDTA, SBTI, aprotinin, and oil per dosage form are 8-16 mg, 150 mg, 65-85 mg, 22-26, and 0.5-0.7 ml, respectively, and the amount of self-emulsifying component is 8-16%. An even more specific embodiment comprises 75 mg SBTI and 24 mg aprotinin. In other embodiments, the above composition further comprises polysorbate 80. In certain embodiments, the polysorbate 80 constitutes 3-10% weight/weight inclusive of the oil-based liquid formulation. In certain embodiments, all the aforementioned ingredients other than the oil are provided in the oil, for example dissolved or suspended in the oil, which is, in some embodiments, one of the oils mentioned herein. Alternatively or in addition, the above composition is coated by a coating that resists degradation in the stomach. Alternatively or in addition, purified KTI3 is present in place of SBTI in one of the amounts mentioned above. In various embodiments, purified BBI is the only protease inhibitor present and is present in an amount of 50-200 mg, in other embodiments 75-200 mg, in other embodiments 75-180 mg, in other embodiments 75-150 mg, in other embodiments 75-125 mg, in other embodiments 90-110 mg, in other embodiments 100-150 mg, in other embodiments 110-140 mg, in other embodiments 120-130 mg, in other embodiments 120-160 mg, in other embodiments 130-150 mg, in other embodiments 75 mg, in other embodiments 100 mg, in other embodiments 125 mg, in other embodiments 150 mg, in other embodiments 175 mg, in other embodiments 200 mg.

"Weight/weight" percentages referred to herein in the context of emulsifiers and detergents utilize the amount of oil base in the formulation, for example fish oil, as the denominator; thus, 60 mg of Gelucire (for example) in 500 mg oil is considered as 12% w/w, regardless of the weight of the other components. Similarly, 50 mg. Tween-80 mixed with 500 mg oil is considered as 10% Tween-80.

In other embodiments, a liquid formulation utilized in the described method or composition is water-free. If more than one liquid formulation is present, for example in a multi-component composition, each liquid formulation may be water-free. "Water-free" refers, in certain embodiments, to a formulation into which no aqueous components have been intentionally added. It does not preclude the presence of trace amounts of water that have been absorbed from the atmosphere into the components thereof. In another embodiment, the liquid formulation is free of aqueous components. If more than one liquid formulation is present, for example in a multi-component composition, each liquid formulation may be free of aqueous components. In yet other embodiments, one or more oils selected from selected from olive oil, flaxseed oil, sesame oil, avocado oil, walnut oil, canola oil, and fish oil are the only liquid components of each of the one or more liquid formulations. In yet another embodiment, fish oil is the only liquid component of each of the one or more liquid formulations. In still another embodiments, the only liquid component of the one or more liquid formulations is selected from the group consisting of fish oil, canola oil, and flaxseed oil.

In other embodiments, a formulation utilized in the described methods and compositions is a solid formulation that comprises insulin, a GLP-1 analogue, EDTA, and at least one trypsin inhibitor. In more specific embodiments, the GLP-1 analogue may be exenatide. In other embodiments, the formulation comprises insulin, a GLP-1 analogue, EDTA, and at least one chymotrypsin inhibitor. In other embodiments, the formulation comprises insulin, a GLP-1 analogue, EDTA, at least one trypsin inhibitor, and at least one chymotrypsin inhibitor. In other embodiments, the formulation comprises insulin, a GLP-1 analogue, EDTA, one trypsin inhibitor, and one chymotrypsin inhibitor. In more specific embodiments, the protease inhibitors are SBTI and aprotinin. Alternatively, purified KTI3 and aprotinin are utilized. In various embodiments, purified BBI is the only protease inhibitor present and is present in an amount of 50-200 mg, in other embodiments 75-200 mg, in other embodiments 75-180 mg, in other embodiments 75-150 mg, in other embodiments 75-125 mg, in other embodiments 90-110 mg, in other embodiments 100-150 mg, in other embodiments 110-140 mg, in other embodiments 120-130 mg, in other embodiments 120-160 mg, in other embodiments 130-150 mg, in other embodiments 75 mg, in other embodiments 100 mg, in other embodiments 125 mg, in other embodiments 150 mg, in other embodiments 175 mg, in other embodiments 200 mg. Alternatively or in addition, the solid formulation is coated with an enteric coating.

The term "solid formulations" as used herein relates to tablets, capsules, and other dosage forms having a non-liquid structure throughout the dosage form. In certain, non-limiting embodiments, the therapeutic peptide(s), EDTA, and protease inhibitor(s), all in crystalline form, or in other embodiments in amorphous form, are combined and subjected to a tableting process known in the art.

In other embodiments, a formulation utilized in the described methods and compositions is a solid formulation that comprises a GLP-1 analogue, EDTA, and at least one trypsin inhibitor. In more specific embodiments, the GLP-1 analogue may be exenatide. In other embodiments, the formulation comprises a GLP-1 analogue, EDTA, and at least one chymotrypsin inhibitor. In other embodiments, the formulation comprises a GLP-1 analogue, EDTA, at least one trypsin inhibitor, and at least one chymotrypsin inhibitor. In other embodiments, the formulation comprises a GLP-1 analogue, EDTA, one trypsin inhibitor, and one chymotrypsin inhibitor. In more specific embodiments, the protease inhibitors are SBTI and aprotinin. Alternatively, purified KTI3 and aprotinin are utilized. In still other embodiments, purified BBI is the only protease inhibitor present. Alternatively or in addition, the liquid formulation is in a gelatin capsule. In more specific embodiments, the gelatin capsule is coated with an enteric coating.

In other embodiments, a formulation utilized in the described methods and compositions is a solid formulation that comprises insulin, EDTA, and at least one trypsin inhibitor. In other embodiments, the formulation comprises insulin, EDTA, and at least one chymotrypsin inhibitor. In other embodiments, the formulation comprises insulin, EDTA, at least one trypsin inhibitor, and at least one chymotrypsin inhibitor. In other embodiments, the formulation comprises insulin, EDTA, one trypsin inhibitor, and one chymotrypsin inhibitor.

In more specific embodiments, the protease inhibitors are SBTI and aprotinin. Alternatively, purified KTI3 and aprotinin are utilized. In still other embodiments, purified BBI is the only protease inhibitor present. Alternatively or in addition, the liquid formulation is in a gelatin capsule. In more specific embodiments, the gelatin capsule is coated with an enteric coating.

Diabetes and Other Metabolic Disorders

Also provided herein is a solid pharmaceutical formulation described herein for treating diabetes mellitus, which is in some embodiments type I DM and is in other embodiments type II DM. Also provided is a method for treating diabetes mellitus by administering to a subject a solid pharmaceutical formulation described herein. In certain embodiments, the pharmaceutical composition is administered to the subject one or more times per day, depending on blood sugar levels. In other embodiments, the pharmaceutical composition is administered to the subject for an extended time.

In other embodiments is provided a solid pharmaceutical formulation described herein, comprising, in various embodiments, insulin, a GLP-1 analogue, or a combination thereof as the active ingredient, for inhibiting or reducing the development of type II diabetes mellitus (T2DM) in a subject at risk thereof. In certain embodiments, the subject at risk is considered "pre-diabetic" and/or exhibits impaired glucose tolerance (IGT). IGT is typically considered to be present when fasting plasma glucose (FPG) levels are between 100-126 milligrams per deciliter (mg/dl) and/or 2-hour values in the oral glucose tolerance test (OGTT) are between 140-200 mg/dl; while T2DM is considered to be present based upon a FPG value of >126 or a 2-hour OGTT value of >200 mg/dl. However, those skilled in the art will appreciate that the exact standards for determining IGT and T2DM are not critical, and other tests, e.g. the frequently sampled intravenous glucose tolerance test (FSIVGTT) and HbA1C levels, may be utilized. In other embodiments, the subject at risk exhibits insulin resistance, obesity, and/or a family history of diabetes. In certain embodiments, the pharmaceutical composition is administered for an extended time. In more specific embodiments, the pharmaceutical composition may be administered for an extended time daily, for example once daily or twice daily. A non-limiting example of daily administration is a single dose before bedtime.

Also provided herein is a solid pharmaceutical formulation described herein for reducing food intake. Also provided is a method for reducing food intake by a subject, by administering to the subject a solid pharmaceutical formulation described herein.

Also provided herein is a solid pharmaceutical formulation described herein for enhancing insulin secretion. Also provided is a method for enhancing insulin secretion by administering to a subject a solid pharmaceutical formulation described herein. In certain embodiments, the pharmaceutical composition is administered to the subject one or more times per day, depending on blood sugar levels. In other embodiments, the pharmaceutical composition is administered to the subject for an extended time.

Also provided herein is a solid pharmaceutical formulation described herein for prophylactically reducing the incidence of hyperglycemia. Also provided is a method for prophylactically reducing hyperglycemia by administering to a subject a solid pharmaceutical formulation described herein. In certain embodiments, the pharmaceutical composition is administered to the subject one or more times per day, depending on blood sugar levels. In other embodiments, the pharmaceutical composition is administered to the subject for an extended time.

Also provided herein is a solid pharmaceutical formulation described herein for prophylactically reducing glucagon secretion. Also provided is a method for prophylactically reducing glucagon secretion by administering to a subject a solid pharmaceutical formulation described herein.

Also provided herein is a pharmaceutical formulation having a particular w/w ratio of BBI to KTI in the pharmaceutical composition, comprising, in various embodiments, insulin, a GLP-1 analogue, or a combination thereof as the active ingredient, for treating diabetes mellitus (DM), which is in some embodiments Type I DM, and is in other embodiments Type II DM. Also provided is a method for treating DM by administering to a subject a pharmaceutical formulation with a particular BBI:KTI w/w ratio. In certain embodiments, the pharmaceutical composition is administered to the subject one or more times per day, depending on blood sugar levels. In other embodiments, the pharmaceutical composition is administered to the subject for an extended time. The pharmaceutical composition is, in various embodiments, a liquid pharmaceutical formulation described herein or a solid pharmaceutical formulation described herein. The aforementioned w/w ratio of BBI to KTI is, in some embodiments, between 1.5:1 and 2.5:1, in other embodiments between 1.6:1 and 2.4:1, in other embodiments between 1.7:1 and 2.3:1, in other embodiments between 1.8:1 and 2.2:1, in other embodiments between 1.9:1 and 2.1:1, in other embodiments between 1.95:1 and 2.05:1, in other embodiments 2:1.

In other embodiments is provided a pharmaceutical formulation having a particular BBI:KTI w/w ratio, comprising, in various embodiments, insulin, a GLP-1 analogue, or a combination thereof as the active ingredient, for inhibiting or reducing the development of (T2DM) in a subject at risk thereof. In certain embodiments, the subject at risk is considered "pre-diabetic", exhibits IGT, exhibits obesity, and/or has a family history of diabetes. In certain embodiments, the pharmaceutical composition is administered for an extended time. In more specific embodiments, the pharmaceutical composition may be administered for an extended time daily, for example once daily or twice daily. A non-limiting example of daily administration is a single dose before bedtime. The aforementioned w/w ratio of BBI to KTI is, in some embodiments, between 1.5:1 and 2.5:1, in other embodiments between 1.6:1 and 2.4:1, in other embodiments between 1.7:1 and 2.3:1, in other embodiments between 1.8:1 and 2.2:1, in other embodiments between 1.9:1 and 2.1:1, in other embodiments between 1.95:1 and 2.05:1, in other embodiments 2:1.

Coatings

In certain embodiments, the described liquid formulation is contained within a capsule, for example a gelatin capsule, which is more specific embodiments itself coated with a pH-sensitive coating. In other embodiments, a solid formulation, for example, may be coated directly with a pH-sensitive coating. Those of skill in the art will appreciate, given the present disclosure, that various pH-sensitive coatings may be utilized in the described methods and compositions. In certain embodiments, any coating that inhibits digestion of the composition in the stomach of a subject may be utilized. Typically, such coatings will not dissolve in human gastric juices within 2 hours, and will dissolve within 30 minutes in duodenal fluid.

In other embodiments, the coating comprises a biodegradable polysaccharide. In other embodiments, a hydrogel is utilized. In other embodiments, the coating comprises one of the following excipients: chitosan, an aquacoat ECD coating, an azo-crosslinked polymer, cellulose acetate phthalate, cellulose acetate trimellitate (CAT), cellulose acetate butyrate, hydroxypropylmethyl cellulose phthalate, or poly vinyl acetate phthalate.

In other embodiments, a timed-release system such as Pulsincap™ is utilized.

In preferred embodiments, the coated dosage forms described herein release the core (containing the oil-based formulation) when pH reaches the range found in the intestines, which is alkaline relative to that in the stomach. In more specific embodiments, the coating comprises a pH-sensitive polymer. In various embodiments, either mono-layer or multi-layer coatings may be utilized.

In one embodiment, the coating is an enteric coating. Methods for enteric coating are well known in the art (see, for example, Siepmann F et al 2005). In more specific embodiments, a Eudragit™ coating is utilized as the enteric coating. Eudragit™ coatings are acrylic polymers, the use of which is well known in the art.

In another embodiment, microencapsulation is used as a stomach-resistant coating in the compositions described herein. Methods for microencapsulation are well known in the art, and are described inter alia in United States Patent Application Publication No. 2011/0305768, which is incorporated by reference herein.

In other embodiments, the described pharmaceutical composition is in the form of a capsule. Gelatin capsules are most preferred, which may be soft gelatin capsules, or in other embodiments hard gelatin capsules. Methods for inserting an oil-based formulation into a gelatin capsule are well known in the art. In more specific embodiments, the gelatin capsule is itself coated by an enteric coating.

A variety of oral dosage forms, such as tablets, capsules, pills, powders, and granules, may be used in the described solid compositions. Suitable excipients can be chosen among, but are not restricted to, solid powdered carriers, e.g. US Pharmacopeia and the Handbook of Pharmaceutical Excipients, for example mannitol, microcrystalline cellulose, calcium hydrogen phosphate, calcium sulphate, and starch; binders, e.g., polyvinylpyrrolidone, starch and hydroxypropyl methylcellulose; disintegrants, e.g., sodium croscarmellose, sodium starch glycollate and polyvinylpyrrolidone as well as lubricating agents, e.g., magnesium stearate, sodium stearyl fumarate, talc and hydrogenated vegetable oil such as Sterotex NF. In some embodiments, lactose-free compositions contain active ingredients, a binder/filler, and a lubricant in compatible amounts. More specific embodiments of lactose-free dosage forms contain active ingredients, microcrystalline cellulose, pre-gelatinized starch, and magnesium stearate. The mixture is then processed, in certain embodiments, into tablets or granules for capsules. In certain embodiments, rapid disintegrating tablets are utilized, which are in some embodiments useful for elderly or infirm individuals who have difficulty swallowing. In other embodiments, the oral dosage form is enteric-coated.

Wherever alternatives for single separable features such as, for example, an insulin protein or dosage thereof, a GLP-1 analogue or dosage thereof, a protease inhibitor or amount thereof, a chelator or amount thereof, an emulsifier or amount thereof, a non-ionic detergent or an amount thereof, or a capsule and/or coating are set forth herein as "embodiments", it is to be understood that such alternatives may be combined freely to form discrete embodiments of the invention disclosed herein.

With respect to the jurisdictions allowing it, all patents, patent applications, and publications mentioned herein, both supra and infra, are incorporated herein by reference.

The invention is further illustrated by the following examples and the figures, from which further embodiments and advantages can be drawn. These examples are meant to illustrate the invention but not to limit its scope.

EXPERIMENTAL DETAILS SECTION

In all the animal experiments described herein, liquid dosage forms that are administered to a human in an enteric-coated capsule may, for example, be administered directly to the digestive system of the animal via a cannula. In general, liquid and solid dosage forms may be fed to animals via gavage.

Example 1: Testing of Oral GLP-1 Analogue and/or Insulin Formulations for Treating NAFLD Volunteers with NAFLD are administered one or more dosage forms having a pH-sensitive coating and/or capsule containing one or more protease inhibitors; EDTA; and a GLP-1 analogue, on an ongoing basis, for example for a time period of between 1-24 months. In other experiments, the dosage form contains insulin and a GLP-1 analogue. In still other experiments, subjects at risk of developing NAFLD are treated with the composition. The NAFLD status of the subjects is followed over the experimental period, to test the effectiveness of the compositions.

Example 2: Testing of Oral GLP-1 Analogue and/or Insulin Formulations for Other Metabolic Indications Volunteers with metabolic disorder (Grundy et al, 2004) are administered one or more dosage forms having a pH-sensitive coating and/or capsule and containing one or more protease inhibitors; EDTA; and a GLP-1 analogue, on an ongoing basis, for example for a time period of 1-24 months. In other experiments, the dosage form contains insulin and a GLP-1 analogue. In still other experiments, subjects at risk of developing metabolic disorder are treated with the composition. Subjects are followed over the experimental period for obesity (for example by measuring waist circumference), total cholesterol levels, hypertriglyceridemia, serum ApoB levels, total cholesterol/HDL ratios, ApoB/ApoA1 ratios, atherosclerosis, sub-clinical inflammation (as can be measured inter alia by measuring levels of C-reactive protein), the presence of a prothrombotic state (as can be measured inter alia by measuring levels of plasminogen activator inhibitor-1 [PAI-1]), the presence of platelet activation, the presence of endothelial dysfunction, the presence of a cardioembolic state, and/or insulin-induced enhancement of vasodilator responses (Sung et al, 2012; Chatrath et al 2012; Nseir et al, 2011).

Example 3: Testing of Oral GLP-1 Analogue Formulations for Treating and Preventing Alzheimer's Disease in an Animal Model One or more dosage forms containing one or more protease inhibitors, EDTA, and a GLP-1 analogue is administered on an ongoing basis, for example for a time period of between 1-24 weeks, to experimental animals in the context of an animal model of Alzheimer's disease. In other experiments, the formulation contains insulin and a GLP-1 analogue as the active agents. In some experiments, the animal model is a streptozotocin (STZ)-induced rat model of AD. Intracerebral injection of STZ leads to hyper-phosphorylation of tau protein and causes a condition that mimics AD. Some experiments utilize sham-injected animals, whereby CSF is used instead of STZ, as a control group.

After complete recovery from the procedure (typically several months after induction), animals are divided into groups and for treatment with oral GLP-1 or empty carrier (e.g. normal saline) for a period of several days, in some experiments for at least 30 days.

Dose-dependent and time-course effects of oral GLP-1 on memory retention are measured during the course of treatment. Following treatment, the animals are sacrificed, and brain tissues are used to evaluate hippocampal and cortical GLP-1 levels, amyloid beta (Aβ) burden, tau phosphorylation, and inflammatory markers.

In some experiments, the cognitive status of the subjects is followed over the experimental period, or neurodegenerative disease status is assessed according to Salcedo et al or a reference cited therein, to test the effectiveness of the compositions. Below are some representative protocols that can be used:

Radial Arm Maze (RAM) Task

Working memory in animals is tested with the RAM apparatus (Alamed) and using described test methods including training. The test is typically performed several months after STZ induction.

Hole-Board (HB) Task

Animals are tested for learning deficits in a food-motivated complex HB apparatus. The apparatus consists of an open field containing an array of holes surrounded by Plexiglass walls. Each hole contains a metal cup with a perforated bottom under which food pellets are placed. The test records the number of visits to food-baited holes (hits), the number of visits to unbaited holes (errors) and the time to complete the trial.

Biochemical Studies

Animals are euthanized at the completion of behavioral studies, and biochemical studies and histology are conducted on fixed brains. In some experiments, the hippocampus and frontal cortex from one hemisphere are dissected and used for biochemical studies, such as those listed below.

Estimation of Active GLP-1 Levels

Isolated hippocampal and cortex samples are homogenized with a 10-fold volume of chilled 50 mM phosphate-buffered saline (pH 7.8). The homogenate is divided into four equal portions and utilized for the estimation of GLP-1, Aβ42, tau and inflammatory markers. Active GLP-1 and Aβ42 levels can be tested using commercially available ELISA kits.

Measurement of Phosphorylated Tau (p-tau)

Hippocampal and cortical tissues are harvested and subjected to Western Blot analysis.

Measurement of TNF-α and IL-1β Levels

TNF-α and IL-4β levels in the hippocampal and cortex homogenate can be measured using available ELISA kits.

Histology and Neuronal Count

The hippocampus and cortex is sectioned and stained with cresyl violet (CV) acetate, and stained neurons are analyzed using an image analyzer. CV positive neurons numbers are compared with the sham control group, and average cell counts of the sections are obtained from each animal.

Example 4: Testing of Oral GLP-1 Analogue Formulations for Treating and Preventing Stroke in an Animal Model The preventive and therapeutic effects of oral GLP-1 analogue are tested in an animal stroke model. One such model is a reperfusion injury model in rats, where rats undergo temporary occlusion of the middle cerebral artery for 90 min. Rats are administered GLP-1 analogue or carrier for several days prior and/or after reperfusion. Assessment of the neurological consequences, biochemical changes, and/or size of infarct is performed. Neurological function may be determined using a modified Bederson's test at one or several time points after occlusion, after which rats may be euthanized for histological investigation. In some experiments, peripheral blood is obtained for measurement of blood glucose level and evaluation of oxidative stress and/or brain tissues are collected to measure vascular endothelial growth factor (VEGF) levels (Sato et al).

Example 5: Testing of Oral GLP-1 Analogue Formulations for Treating and Preventing Parkinson's Disease Patients with moderate Parkinson's disease (PD) are randomly assigned to receive either oral GLP-1 analogue or placebo for 12 months. PD progression is measured, in some cases after withdrawal of conventional PD medication. For example, the Movement Disorders Society Unified Parkinson's Disease Rating Scale (MDS-UPDRS) may be used, in some cases together with one or more non-motor tests, at several time points during treatment and in some cases after a further washout period (Aviles-Olmos et al).

Example 6: Testing of Oral GLP-1 Analogue Formulations for Treating and Preventing Traumatic Brain Injury (TBI) in an Animal Model The ability of oral GLP-1 analogue formulations to protect against or facilitate recovery from TBI is evaluated. In some experiments, the GLP-1 analogue is administered for several days after injury. One model that may be used is an in vivo fluid percussion injury model (Eakin et al). Markers of cell death and measures of cognitive function may be utilized. Examples of the latter are the Morris Water Maze and other cognitive tests described herein.

Example 7: Testing of Oral GLP-1 Analogue Formulations for Treating and Preventing Peripheral Nerve Injury in an Animal Model The ability of oral GLP-1 analogue formulations to protect against or facilitate recovery from peripheral nerve disease is evaluated. One model that may be used is sciatic nerve crush nerve injury. GLP-1 analogue or empty carrier is administered shortly after crush injury and continued for several subsequent days or weeks. Rats subjected to sciatic nerve crush may exhibit marked functional loss, electrophysiological dysfunction, and atrophy of the tibialis anterior muscle (TA). Recovery can be monitored by measuring neurological function, electrophysiological function, muscle atrophy, and/or morphological parameters several days or weeks after nerve crush (Yamamoto et al).

Example 8: Testing of Oral GLP-1 Analogue Formulations for Treating and Preventing Cognition and Mood Disorders In other experiments, the ability of oral GLP-1 analogue formulations to treat bipolar disorder, major depressive disorder, schizophrenia, and/or schizoaffective disorder is evaluated. Individuals with these conditions or at risk of developing them are treated with GLP-1 analogue on an ongoing basis, for example for a time period of between 1-24 months, and clinical global improvement in psychiatric symptoms and/or manic, depressive, or schizophrenic symptoms is measured. In other experiments, cognitive function is determined, using tests known to those skilled in the art (McIntyre et al).

Example 9: Testing of Oral GLP-1 Analogue Formulations for Treating and Preventing Amyotrophic Lateral Sclerosis (ALS) in an Animal Model In other experiments, the ability of oral GLP-1 analogue formulations to treat or prevent ALS is evaluated. GLP-1 analogue is administered on an ongoing basis, for example for between 1-18 weeks. In some experiments, an animal model such as the SOD1 G93A mutant mouse (Li et al) is utilized. Disease progression can be monitored by measuring activity level, e.g. running behavior, lumbar spinal cord structure, and, using brain tissue, neuron density and specific disease progression markers such as glial fribrillary acidic protein (GFAP), Caspase-3, Choline acetyl transferase (ChAT), and the neuronal cell neurofilament protein, SMI-32 (Li et al).

Example 10: Testing of Oral GLP-1 Analogue Formulations for Treating and Preventing Huntington'S Disease in an Animal Model In other experiments, the ability of oral GLP-1 analogue formulations to treat or prevent Huntington's disease is evaluated. GLP-1 analogue is administered on an ongoing basis, for example for between 1-18 weeks. In some experiments, an animal model such as those described in Brooks and Dunnett and the references cited therein is utilized.

Example 11: Testing of Oral GLP-1 Analogue Formulations for Treating and Preventing Diabetic Neuropathy in an Animal Model In other experiments, the ability of oral GLP-1 analogue formulations to treat or prevent diabetic neuropathy is evaluated. GLP-1 analogue is administered on an ongoing basis, for example for between 1-18 weeks. In some experiments, an animal model such as those described in Lai and Lo and the references cited therein is utilized.

Example 12: Testing of Oral GLP-1 Analogue Formulations for Treating and Preventing Alzheimer'S Disease, Huntington'S Disease, Stroke, TBI, Peripheral Nerve Injury, AL, and Diabetic Neuropathy in Humans One or more dosage forms containing one or more protease inhibitors, EDTA, and a GLP-1 analogue is administered on an ongoing basis, for example for between 1-48 months, to subjects at risk of developing Alzheimer's disease, Huntington's disease stroke, TBI, peripheral nerve injury, ALS, or diabetic neuropathy. In other experiments, the formulation contains insulin and a GLP-1 analogue. To test the effectiveness of the compositions, the disease status of the subjects is followed over the experimental period, in some cases in combination with brain imaging. Disease status may be followed, for example, by performing physiological tests and/or determining cognitive status or neurological function, according to Salcedo et al or a reference cited therein, or other tests known to those skilled in the art.

Example 13: Testing of Oral GLP-1 Analogue Formulations for Treating and Preventing Diabetic Neuropathy in an Animal Model In other experiments, the ability of solid pharmaceutical formulations, containing insulin, a GLP-1 analogue, or a combination thereof, to inhibit or prevent the development of Type II Diabetes Mellitus (T2DM) in a subject with impaired glucose tolerance (IGT) is evaluated.

The pharmaceutical composition is administered on an ongoing basis, for example for between 1-240 weeks, in some experiments daily at bedtime. Patients are followed by DM indicia known in the art, such as fasting plasma glucose (FPG) levels, frequently sampled intravenous glucose tolerance test (FSIVGTT), oral glucose tolerance test (OGTT), and HbA1C levels, to monitor the development of T2DM. Alternatively or in addition, insulin sensitivity and beta-cell function are measured.

In the claims, the word "comprise", and variations thereof such as "comprises", "comprising", and the like indicate that the components listed are included, but not generally to the exclusion of other components.

REFERENCES

Alamed et al. Two-day radial-arm water maze learning and memory task; robust resolution of amyloid-related memory deficits in transgenic mice. Nat Protoc. 2006; 1(4): 1671-9.

Aviles-Olmos et al. Exenatide and the treatment of patients with Parkinson's disease. J Clin Invest. 2013; 123(6): 2730-2736.

Ben-Shlomo et al, Glucagon-like peptide-1 reduces hepatic lipogenesis via activation of AMP-activated protein kinase. J Hepatol. 2011 June; 54(6): 1214-23.

Brooks and Dunnett. Mouse Models of Huntington's Disease. Curr Top Behav Neurosci. 2013 Dec. 20. [Epub ahead of print].

Centis E, Marzocchi R, Di Domizio S, Ciaravella M F, Marchesini G (2010) The effect of lifestyle changes in non-alcoholic fatty liver disease. Dig Dis 28: 267-273.

Chatrath et al. Dyslipidemia in patients with nonalcoholic fatty liver disease. Semin Liver Dis. 2012 February; 32(1): 22-9. doi: 10.1055/s-0032-1306423.

Chiquette E et al. Treatment with exenatide once weekly or twice daily for 30 weeks is associated with changes in several cardiovascular risk markers. Vasc Health Risk Manag. 2012; 8:621-9.

Eakin et al. Exendin-4 ameliorates traumatic brain injury-induced cognitive impairment in rats. PLoS One. 2013 Dec. 2; 8(12):e82016.

Eldor R, Kidron M, Arbit E. A single-blind, two-period study to assess the safety and pharmacodynamics of an orally delivered GLP-1 analog (exenatide) in healthy subjects. American Diabetes Association 70$^{th}$ Annual Scientific Sessions, Jun. 25-29, 2010.

Grundy et al. Definition of metabolic syndrome: report of the National Heart, Lung, and Blood Institute/American Heart Association conference on scientific issues related to definition. Arterioscler Thromb Vasc Biol. 2004 February; 24(2):e13-8.

Richard A C Hughes (23 Feb. 2002). "Clinical review: Peripheral neuropathy". British Medical Journal 324:466.

Juurinen et al. Effects of insulin therapy on liver fat content and hepatic insulin sensitivity in patients with type 2 diabetes. Am J Physiol Endocrinol Metab. 2007 March; 292(3):E829-35

Kertes P J, Johnson T M, ed. (2007). Evidence Based Eye Care, Philadelphia, Pa.: Lippincott Williams & Wilkins.

Kim et al, When GLP-1 hits the liver: a novel approach for insulin resistance and NASH. Am J Physiol Gastrointest Liver Physiol. 2012 Apr. 15; 302(8): G759-61.

Lai and Lo. Animal models of diabetic retinopathy: summary and comparison. J Diabetes Res. 2013; 2013: 106594.

Li et al. Exendin-4 ameliorates motor neuron degeneration in cellular and animal models of amyotrophic lateral sclerosis. PLoS One. 2012; 7(2):e32008.

López-Delgado et al. Effects of glucagon-like peptide 1 on the kinetics of glycogen synthase a in hepatocytes from normal and diabetic rats. Endocrinology 1998; 139:2811-2817.

Malhi H, Gores G J (2008) Molecular mechanisms of lipotoxicity in nonalcoholic fatty liver disease. Semin Liver Dis 28: 360-369.

Martinez-Colubi M et al, Switching to darunavir/ritonavir monotherapy (DRV/r mx): effect on kidney function and lipid profile. J Int AIDS Soc. 2012 Nov. 11; 15(6): 18348. doi: 10.7448/IAS.15.6.18348.

Mazhar et al. Noninvasive assessment of hepatic steatosis. Clin Gastroenterol Hepatol. 2009 February; 7(2): 135-40. doi: 10.1016/j.cgh.2008.11.023.

McIntyre et al. The neuroprotective effects of GLP-1: possible treatments for cognitive deficits in individuals with mood disorders. Behav Brain Res. 2013 Jan. 15; 237:164-71.

Miyashita T et al, Hepatoprotective effect of tamoxifen on steatosis and non-alcoholic steatohepatitis in mouse models. J Toxicol Sci. 2012; 37(5): 931-42

Nielsen et al. Effects of exenatide on diabetes, obesity, cardiovascular risk factors, and hepatic biomarkers in patients with type 2 diabetes. J Diabetes Sci Technol. 2008 March; 2(2):255-60.

Nseir et al. Mechanisms linking nonalcoholic fatty liver disease with coronary artery disease. Dig Dis Sci. 2011 December; 56(12): 3439-49.

Puri P, Mirshahi F, Cheung O, Natarajan R, Maher J W, et al. (2008) Activation and dysregulation of the unfolded protein response in nonalcoholic fatty liver disease. Gastroenterology 134: 568-576.

Redondo et al. Cell signalling of the GLP-1 action in rat liver. Mol Cell Endocrinol 2003; 204:43-50.

Retnakaran R et al. Discordant effects on central obesity, hepatic insulin resistance, and alanine aminotransferase of low-dose metformin and thiazolidinedione combination therapy in patients with impaired glucose tolerance. Diabetes Obes Metab. 2012 January; 14(1): 91-3.

Salcedo et al, Neuroprotective and neurotrophic actions of glucagon-like peptide-1: an emerging opportunity to treat neurodegenerative and cerebrovascular disorders. Br J Pharmacol. 2012 July; 166(5): 1586-99.

Sato et al. Neuroprotective Effects of Liraglutide for Stroke Model of Rats. Int. J. Mol. Sci. 2013, 14, 21513-21524.

Saverymuttu S H, Joseph A E, Maxwell J D. Ultrasound scanning in the detection of hepatic fibrosis and steatosis. Br Med J (Clin Res Ed) 1986; 292:13-15.

Sharma et al. GLP-1 Analogs Reduce Hepatocyte Steatosis and Improve Survival by Enhancing the Unfolded Protein Response and Promoting Macroautophagy. PLoS ONE 2011; 6(9):e25269.

Siepmann F, Siepmann J et al, Blends of aqueous polymer dispersions used for pellet coating: importance of the particle size. J Control Release 2005; 105(3): 226-39.

Sprecher C A, Morgenstern K A, Mathewes S, Dahlen J R, Schrader S K, Foster D C, Kisiel W. J Biol Chem. 1995 December 15; 270(50): 29854-61.

Sun J., Rose J. B., Bird P. (1995) J. Biol. Chem. 270, 16089-16096.

Sung et al. Combined influence of insulin resistance, overweight/obesity, and fatty liver as risk factors for type 2 diabetes. Diabetes Care. 2012 April; 35(4): 717-22

Tesauro et al. Effects of GLP-1 on Forearm Vasodilator Function and Glucose Disposal During Hyperinsulinemia in the Metabolic Syndrome. Diabetes Care. 2012 Oct. 15.

Yamamoto et al. Therapeutic Effect of Exendin-4, a Long-Acting Analogue of Glucagon-Like Peptide-1 Receptor Agonist, on Nerve Regeneration after the Crush Nerve Injury. BioMed Research International Volume 2013 (2013), Article ID 315848.

Younossi et al, Nonalcoholic fatty liver disease in lean individuals in the United States. Medicine (Baltimore). 2012 November; 91(6): 319-27.

---

The invention claimed is:

1. A method for inhibiting the development of or treating nonalcoholic fatty liver disease (NAFLD) in a human subject in need thereof, said method comprising the step of orally administering to the subject a water-free pharmaceutical composition comprising a therapeutic protein that inhibits the development of or treats the subject's NAFLD, a protease inhibitor, and a chelator of divalent cations,
   thereby inhibiting the development of or treating the subject's NAFLD, wherein the therapeutic protein consists of insulin.

2. The method of claim 1, where said pharmaceutical composition is administered for more than one month.

3. The method of claim 1, wherein said pharmaceutical composition is administered once daily or twice daily.

4. The method of claim 1, wherein said pharmaceutical composition comprises a liquid formulation, wherein said insulin, said protease inhibitor, and said chelator of divalent cations are in said liquid formulation.

5. The method of claim 4, wherein said liquid formulation is inside a capsule.

6. The method of claim 5, wherein said capsule is surrounded by a coating that resists degradation in the stomach.

7. The method of claim 4, wherein said liquid formulation is an oil-based liquid formulation.

8. The method of claim 1, wherein said pharmaceutical composition is a solid formulation.

9. The method of claim 1, wherein said insulin is present in said pharmaceutical composition in an amount between 8-32 mg inclusive, per dose for an adult patient or a corresponding amount per body weight for a pediatric patient.

10. The method of claim 1, wherein administering said composition inhibits the development of nonalcoholic fatty liver disease (NAFLD).

11. The method of claim 10, where said pharmaceutical composition is administered for more than one month.

12. The method of claim 10, wherein said pharmaceutical composition is administered once daily or twice daily.

13. The method of claim 10, wherein said insulin is present in said pharmaceutical composition in an amount between 6-14 mg inclusive, per dose for an adult patient or a corresponding amount per body weight for a pediatric patient.

14. The method of claim 1, wherein administering said composition treats the nonalcoholic fatty liver disease (NAFLD).

15. The method of claim 14, where said pharmaceutical composition is administered for more than one month.

16. The method of claim 14, wherein said pharmaceutical composition is administered once daily or twice daily.

17. The method of claim 14, wherein said insulin is present in said pharmaceutical composition in an amount between 6-14 mg inclusive, per dose for an adult patient or a corresponding amount per body weight for a pediatric patient.

18. A method for inhibiting the development of or treating nonalcoholic fatty liver disease (NAFLD) in a non-human subject in need thereof, said method comprising the step of orally administering to the non-human subject a water-free pharmaceutical composition comprising a therapeutic protein that inhibits the development of or treats the subject's NAFLD, a protease inhibitor, and a chelator of divalent cations,
   thereby inhibiting the development of or treating the subject's NAFLD, wherein the therapeutic protein consists of insulin.

19. The method of claim 18, where said pharmaceutical composition is administered for more than one month.

* * * * *

UNITED STATES PATENT AND TRADEMARK OFFICE
CERTIFICATE OF CORRECTION

Page 1 of 1

PATENT NO. : 10,967,051 B2
APPLICATION NO. : 16/195184
DATED : April 6, 2021
INVENTOR(S) : Miriam Kidron et al.

It is certified that error appears in the above-identified patent and that said Letters Patent is hereby corrected as shown below:

On the Title Page

Item (30), (Foreign Application Priority Data), delete "PCT/IL2014/050007" and insert -- PCT/IL2013/050007 --, therefor.

Signed and Sealed this
Ninth Day of November, 2021

Drew Hirshfeld
*Performing the Functions and Duties of the
Under Secretary of Commerce for Intellectual Property and
Director of the United States Patent and Trademark Office*